US012638384B2

(12) United States Patent
Mahalanabish et al.

(10) Patent No.: US 12,638,384 B2
(45) Date of Patent: May 26, 2026

(54) PLASMONIC NANOSTRUCTURE AND ASSOCIATED CELLULAR IMAGING SYSTEMS AND METHODS

(71) Applicant: Cornell University, Ithaca, NY (US)

(72) Inventors: Aditya Mahalanabish, Ithaca, NY (US); He Huang, Ithaca, NY (US); Gennady Shvets, Ithaca, NY (US)

(73) Assignee: Cornell University, Ithaca, NY (US)

( * ) Notice: Subject to any disclaimer, the term of this patent is extended or adjusted under 35 U.S.C. 154(b) by 179 days.

(21) Appl. No.: 18/409,557

(22) Filed: Jan. 10, 2024

(65) Prior Publication Data

US 2024/0230526 A1     Jul. 11, 2024

Related U.S. Application Data

(60) Provisional application No. 63/438,200, filed on Jan. 10, 2023.

(51) Int. Cl.
| | |
|---|---|
| *G01N 21/35* | (2014.01) |
| *G01N 21/3563* | (2014.01) |
| *G01N 33/483* | (2006.01) |
| *G02B 1/00* | (2006.01) |

(52) U.S. Cl.
CPC ..... *G01N 21/3563* (2013.01); *G01N 33/4833* (2013.01); *G01N 2021/3595* (2013.01); *G02B 1/002* (2013.01); *G02B 2207/101* (2013.01)

(58) Field of Classification Search
CPC .......... G01N 21/3563; G01N 33/4833; G01N 2021/3595
See application file for complete search history.

(56) References Cited

U.S. PATENT DOCUMENTS

| | | |
|---|---|---|
| 9,496,435 B2 | 11/2016 | Wang et al. |
| 10,315,951 B2 | 6/2019 | Toussaint et al. |
| 10,571,606 B2 | 2/2020 | Altug et al. |
| 10,585,040 B2 | 3/2020 | Sykora |
| 10,830,695 B2 | 11/2020 | Perkins |
| 11,220,756 B2 | 1/2022 | Busnaina et al. |

(Continued)

FOREIGN PATENT DOCUMENTS

| | | |
|---|---|---|
| WO | WO 2020008357 A1 | 1/2020 |
| WO | WO 2020095049 A1 | 5/2020 |
| WO | WO 2023158385 A1 | 8/2023 |

OTHER PUBLICATIONS

Grenci et al., "Optimization of microfluidic systems for IRMS long term measurement of living cells" Microelectronic Engineering vol. 98, 2012, pp. 698-702.

(Continued)

*Primary Examiner* — Hugh Maupin
(74) *Attorney, Agent, or Firm* — Cozen O'Connor

(57) ABSTRACT

A plasmonic nanostructure includes a dielectric substrate, a periodic array of dielectric pillars on the dielectric substrate; and, on each dielectric pillar of the periodic array, a respective conductive layer. Each dielectric pillar of the periodic array of dielectric pillars is between the respective conductive layer and the dielectric substrate. A method for imaging a cell includes reflecting an optical beam off the plasmonic nanostructure. The plasmonic nanostructure has biological cells adhered thereto. The method also includes collecting the reflected optical beam with an optical detector.

21 Claims, 18 Drawing Sheets

(56) References Cited

U.S. PATENT DOCUMENTS

| | | | |
|---|---|---|---|
| 2004/0113077 A1* | 6/2004 | Franzen | G01N 21/553 |
| | | | 250/338.1 |
| 2006/0256343 A1* | 11/2006 | Choma | G01N 21/4795 |
| | | | 356/450 |
| 2011/0058164 A1* | 3/2011 | Zhang | G01N 21/658 |
| | | | 356/301 |
| 2013/0040862 A1 | 2/2013 | Li et al. | |
| 2014/0175546 A1 | 6/2014 | Huffaker et al. | |
| 2016/0018263 A1* | 1/2016 | Adato | G01N 21/658 |
| | | | 250/339.02 |
| 2020/0141871 A1* | 5/2020 | Chang | G01N 33/587 |
| 2021/0059574 A1 | 3/2021 | Shinohara et al. | |
| 2021/0080387 A1 | 3/2021 | Shvets et al. | |
| 2021/0239605 A1 | 8/2021 | Altug Yanik et al. | |
| 2021/0302312 A1 | 9/2021 | Shvets et al. | |
| 2022/0310868 A1 | 9/2022 | Takeda et al. | |
| 2024/0410826 A1* | 12/2024 | Wang | G01N 21/47 |

OTHER PUBLICATIONS

Fale et al., "In situ Fourier transform infrared analysis of live cells' response to doxorubicin", Biochimica et Biophysica Acta, vol. 1853, 2015 pp. 2640-2648.

Chan et al., "Label-free in situ quantification of drug in living cells at micromolar levels using infrared spectroscopy", Analytical Chemistry, vol. 86, 2014, pp. 11673-11679.

Huang et al., "Monitoring the effects of chemical stimuli on live cells with metasurface-enhanced infrared reflection spectroscopy", Lab on a Chip, vol. 21, 2021, pp. 3991-4004.

Kelp et al. "Application of metasurface-enhanced infra-red spectroscopy to distinguish between normal and cancerous cell types" Analyst, vol. 144, 2019, pp. 115-1127.

Scott et al., "Label-free whole-cell assays: Expanding the scope of GPCR screening", Drug Discovery Today, vol. 15, 2010, pp. 704-716.

Fang, "Label-free drug discovery", Frontiers in Pharmacology, vol. 5, 2014, pp. 1-8.

Hanson et.al., "Characterization of the Cell-nanopillar Interface by Transmission Electron Microscopy" Nano Letters, vol. 12, 2012, pp. 5815-5820.

Li et al. "A nanostructure platform for live-cell manipulation of membrane curvature" Author Manuscript from Nature Protocols., vol. 14, 2019, pp. 1772-1802.

Vinje et al., "Analysis of Actin and Focal Adhesion Organisation in U2OS Cells on Polymer Nanostructures", Nanoscale Research Letters, vol. 16:143, 2021, 14 pages.

Zhao et al., "Nanoscale manipulation of membrane curvature for probing endocytosis in live cells", Author Manuscript from Nature Nanotech, vol. 12, 2017, pp. 750-756.

Lou et al., "Membrane curvature underlies actin reorganization in response to nanoscale surface topography", Proceedings of the National Academy of Sciences, vol. 116, No. 46, 2019, pp. 23143-23151.

Kazarian et al., "ATR-FTIR spectroscopic imaging: recent advances and applications to biological systems" Analyst, vol. 138, pp. 1940-1951.

Cobb et al., "FT-IR Spectroscopic Analysis of the Secondary Structures Present during the Desiccation Induced Aggregation of Elastin-Like Polypeptide on Silica", ACS Omega, vol. 5, 2020, pp. 8403-8413.

Isensee et al., "Biomedical applications of mid-infrared quantum cascade lasers—a review" Analyst, vol. 143, 2018, pp. 5888-5911.

Bai et al., "Bond-Selective Imaging of Cells by Mid-Infrared Photothermal Microscopy in High Wavenumber Region", Journal of Physical Chemistry B. Author manuscript, 2017, 16 pages.

Zhang et al., "Electrical generation of visible surface plasmon polaritons by a nanopillars antenna array" APL Photonics, vol. 6, 056102, 2021, 7 pages.

Gili et al., "Metal-dielectric hybrid nanoantennas for efficient frequency conversion at the anapole mode", Beilstein Journal of Nanotechnology, vol. 9, 2018, pp. 2306-2314.

Liu et al., "Ultra-tall sub-wavelength gold nano pillars for high sensitive LSPR sensors," Microelectronic Engineering, vol. 196, 2018, pp. 7-12.

Abstract of Haugwitz et al., "Plasmonic dipole nanoantennas on a SiO2/Si substrate and their characterization Undefined," Proceedings of SPIE 10686, Silicon Photonics: From Fundamental Research to Manufacturing, 1068619, May 21, 2018.

* cited by examiner

PLASMONIC NANOSTRUCTURE AND ASSOCIATED CELLULAR IMAGING SYSTEMS AND METHODS

CROSS-REFERENCE TO RELATED APPLICATIONS

This application claims the benefit of U.S. Provisional Application No. 63/438,200, filed on 10 Jan. 2023, the disclosure of which is incorporated herein by reference in its entirety.

GOVERNMENT RIGHTS

This invention was made with government support under Project Numbers 1R21CA251052 and 1R21GM138947 awarded by the National Institute of Health. The government has certain rights in the invention.

BACKGROUND

Infrared (IR) spectroscopy is a popular method for chemical analysis based on the specific molecular vibrations serving as molecular fingerprints. In recent years, IR spectroscopy has seen many applications in the analysis of biological materials, such as biofluids, tissues, and cells. However, due to the strong attenuation of IR light in water, IR spectroscopy of aqueous samples and in particular of live cells in cell culture environment, has been challenging. Currently available techniques for the IR spectroscopy of live cells can be divided into reflection based (RB) and transmission/transflection based (TB). For TB devices, thin flow cells have been used to limit the optical path through water. RB assays based on Attenuated Total Reflection (ATR) spectroscopy have also been developed. None of these techniques can be readily integrated with standard cell culture workflow, making a transition to high-throughput (HT) cell assaying challenging.

SUMMARY OF THE EMBODIMENTS

In a first aspect, a plasmonic nanostructure includes a dielectric substrate, a periodic array of dielectric pillars on the dielectric substrate; and, on each dielectric pillar of the periodic array, a respective conductive layer. Each dielectric pillar of the periodic array of dielectric pillars is between the respective conductive layer and the dielectric substrate.

In a second aspect, a method for imaging a cell is disclosed. The method includes reflecting an optical beam off a plasmonic nanostructure of the first aspect. The plasmonic nanostructure has biological cells adhered thereto. The method also includes collecting the reflected optical beam with an optical detector.

DETAILED DESCRIPTION OF THE EMBODIMENTS

1 Plasmonic Nanostructures

Figure 1:
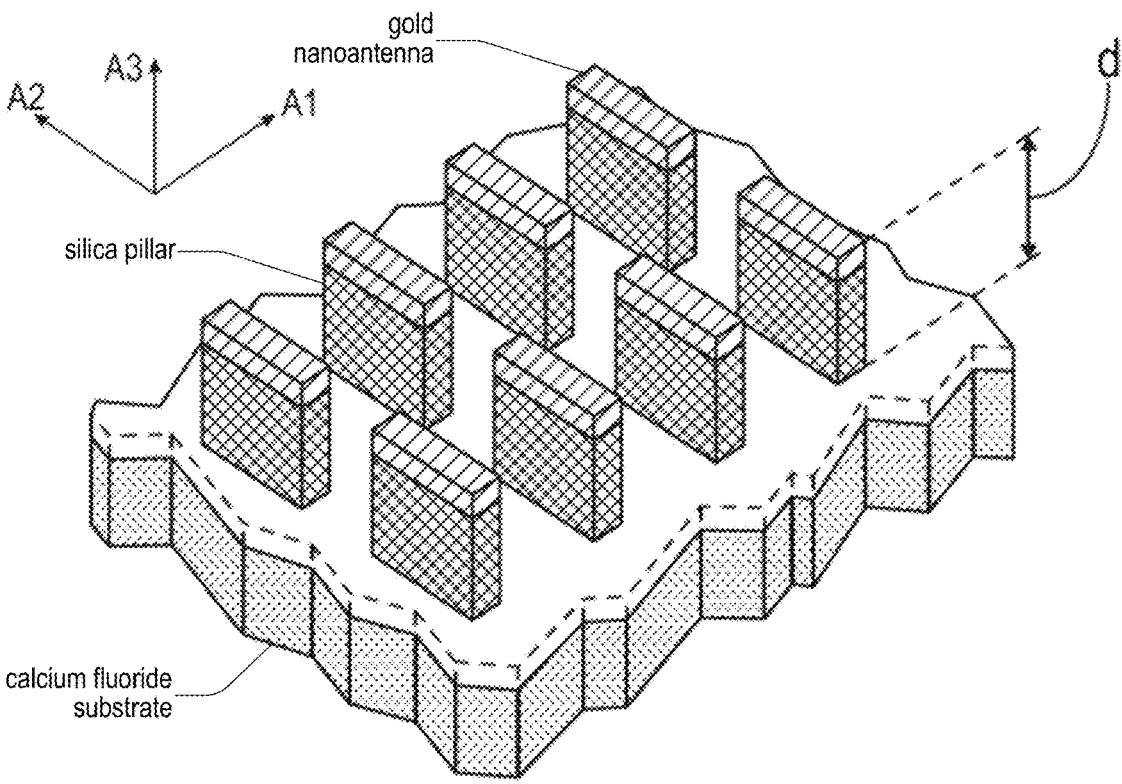
FIG. 1 is a schematic of a 3D plasmonic nanostructure that includes metallic antennas deposited atop of pedestal-type dielectric pillars, in an embodiment.
Figure 2:
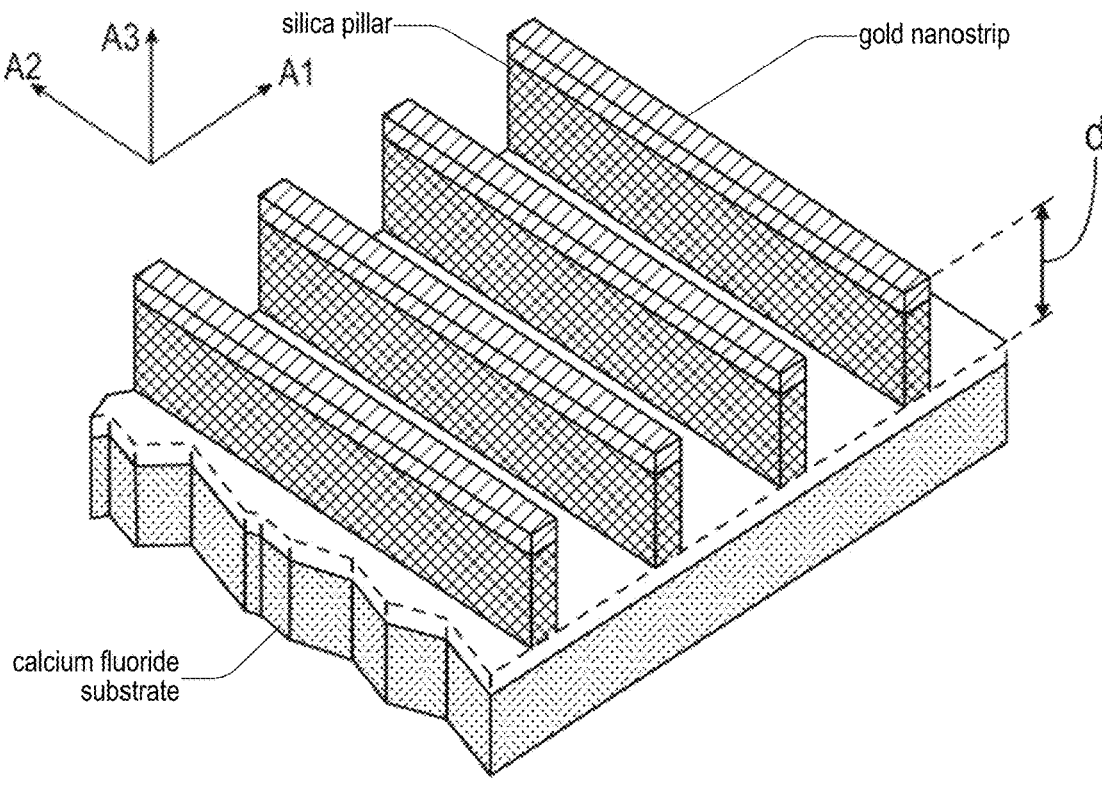
FIG. 2 is a schematic of a 3D plasmonic nanostructure that includes metallic strips (right) deposited atop of dielectric ridges.

Embodiments disclosed herein combine metallic optical nanostructures such as plasmonic nano-antennas and meta-surfaces used for Surface-enhanced infrared absorption (SEIRA) spectroscopy and Metasurface-Enhanced Infrared Spectroscopy (MEIRS), as well as periodic metallic strips (nano-grating), with pedestal-style dielectric protrusions (FIG. 1). The underlying planar substrate that supports the nanostructure may be transparent in the spectral region of interest (i.e., in mid-IR), and may be formed of calcium fluoride. On top of the underlying substrate, the structure may include another dielectric layer forming the pedestal-style dielectric protrusions. The dielectric layer may be formed of silica. The thickness of the protrusions dielectric layer may vary between a few hundred nanometers to a few micrometers. The material composition of the protrusions dielectric layer may be the same as, or different from, the substrate material. The protrusions may be shaped as short (less than several microns) nanopillars (FIG. 1), or long (tens of microns) nanoridges (FIG. 2). Metallic structures are fabricated atop of the dielectric nano-protrusions. Two typical implementations are shown: linear metallic nano-antennas on top of dielectric nanopillars (FIG. 1), or metallic nanostrips on top of dielectric nanoridges (FIG. 2).

The first implementation includes arrays of resonant optical nano-antennas that are matched to specific molecular absorbance bands of cells (e.g., amide bands of protein molecules). Such resonant nano-antennas are fabricated on top of silica nanopillars of the same cross-sectional shape, placed on top of an infrared transparent (e.g. $CaF_2$) substrate. This 3D nanostructure has at least two distinct benefits compared to previously disclosed metasurfaces.

Firstly, when cells wrap around the 3D nanostructure (metallic nano-antenna atop of a dielectric nanopillar) instead of lying flat on top of a 2D nanostructure, there is an increase in metasurface nearfield overlap with the cells. This increases the strength of a reflected IR signal resulting from the presence of the cells atop of a 3D nanostructure. Secondly, cell endocytosis also leads to accumulation of certain proteins like clathrin and actin around the region where the cell membrane curvature takes place (right where the metasurface is located). This, while increasing the amide signal observed by our MEIRS measurement will also make our technique very sensitive to processes that involve changes in actin concentration in cells. A different embodiment (see FIG. 3), where 3D nanostructures are supported by an air-bridged membrane, has an advantage of avoiding mid-IR light propagation through the underlying IR-transparent substrate.

The second implementation shown in FIG. 2 includes a periodic array of long, thin strips of metals on dielectric nanoridges, fabricated on infrared transparent substrates. The nanoridges may be formed of silica. Such arrangement of metallic structures reflect light with polarization along the direction of the metal strips, whereas the orthogonal light polarization is transmitted with minimal reflection. When infrared light is incident from IR-transparent substrate side, it first transmits through the middle layer between dielectric nanoridges. Next, it is reflected by the metal strips, and then transmitted through the middle layer for a second time. When an analyte that can fill the space between the nanoridges (e.g., liquid samples, or live cells that can envelope the dielectric nanopillars) is introduced, infrared light transmits through it twice. This enables a spectroscopic measurement in the transflectance mode.

Such measurement may be compared to total reflection Fourier Transform infrared (ATR-FTIR) spectroscopy. In ATR-FTIR the use of internal reflection elements and specific incidence angles makes it difficult to scale the measurement to multi-well format. In embodiments disclosed herein, the structure is made on top of a planar substrate and light is normally incident from below, making it easier to scale up the measurement for multi-well structures. Another limitation of ATR is that the penetration depth of the probe wave is wavelength-dependent. Therefore, the optical length probed at long wavelengths is longer than that for shorter wavelengths. As a result, the signal-to-noise ratio (SNR) for lipid absorbance (~3000 $cm^{-1}$) is generally low. While amides can be studied efficiently, the ATR approach is sub-optimal for studying changes in lipid composition of the cell.

Figure 4:
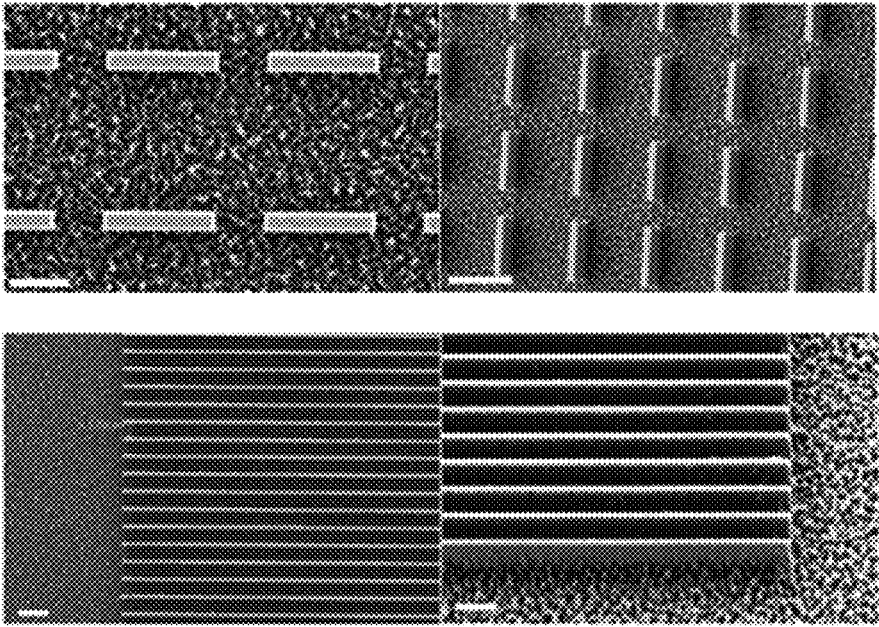
FIG. 4 includes scanning electron microscope images of fabricated devices of FIGS. 1 and 2.

Embodiments disclosed herein circumvent these issues. Because the device is based on transflection, the collected spectra are similar to those obtained from transmissions. The 3D nano-grating device illustrated in FIG. 2 also has a broadband response, where the optical length probed is independent of the wavelength. Therefore, shorter wavelengths (e.g., corresponding to C—H vibrations in lipid molecules) can be probed as efficiently as the longer wavelengths corresponding to, for example, amide vibrations of protein molecules. SEM images of the fabricated devices schematically shown in FIG. 1 are presented in FIG. 4.

1.1 Device Fabrication and Cell Seeding

Figure 3:
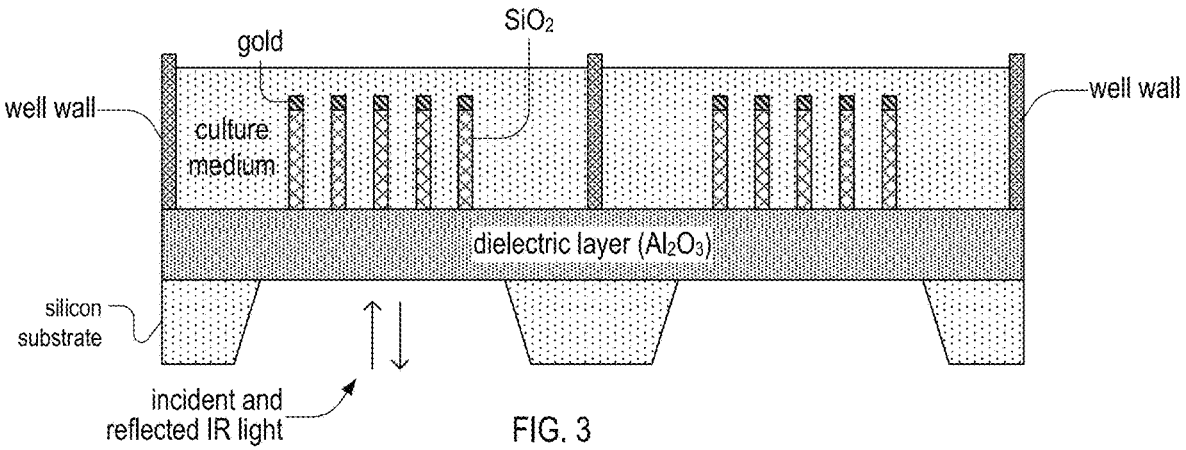
FIG. 3 is a schematic of a 3D nanostructure supported by air-bridged membrane (ABM).

For one specific embodiment shown in FIG. 1, a fabrication process includes depositing a layer of silica (~1 μm) onto IR transparent $CaF_2$ substrates (12.5 mm×12.5 mm), by PECVD process. The silica side is then spin-coated with PMMA 495k A4. A square lattice pattern of nano-antennas (200-nm wide, 1.8-μm long and periodicity of 2.7 μm: see FIG. 1) or a one-dimensional (1D) array of nanoridge (200-nm wide, periodicities between 0.675 μm and 1.35 μm: see FIG. 2) was exposed on the e-beam resist (PMMA) using an e-beam lithography tool (JEOL 9500) and was developed using MIBK:IPA (1:3) solution. 70 nm gold was evaporated into the pattern, with a 5-nm chromium adhesion layer and an 18-nm chromium mask on top, followed by the lift-off process. Following this, we use reactive ion etch (with a mixture of $CF_4$ and Ar) to etch down the silica using the chromium layer as mask. The silica is etched down to form nanopillars of varying heights (700 nm, 850 nm). FIG. 3 shows several representative SEM images of the fabricated embodiments of 3D nanostructures comprising gold nano-antennas atop of silica pillars (top row), or gold nanostrips atop of silica ridges (bottom row).

Live cells may be seeded and grown directly on such a structure kept inside a standard cell culture incubator. Prior to seeding the cells, the samples are sterilized with 70% ethanol. In some embodiments, the samples are coated with appropriate coatings (e.g., fibronectin) that mimic the extracellular matrix (ECM) and improve subsequent cell adhesion and spreading. Cells are then seeded onto this device for spectroscopic measurements. FIG. 3 shows several representative SEM images of the fabricated embodiments of 3D nanostructures comprising gold nano-antennas atop of silica pillars (top row), or gold nanostrips atop of silica ridges (bottom row).

1.2 Implementation and Results for Elevated Plasmonic Nanostructures

Figure 5:
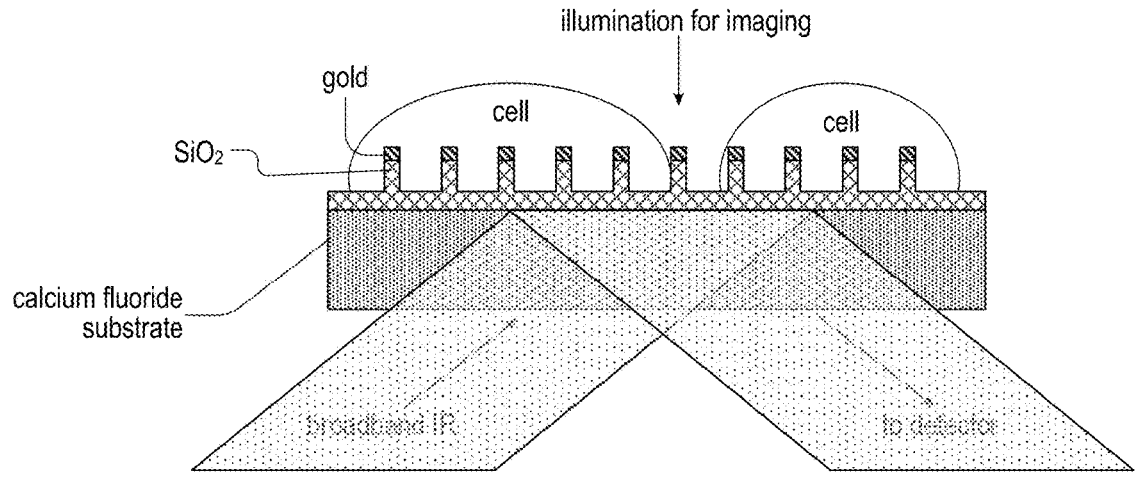
FIG. 5 is a schematic of an optical measurement setup for optical measurement using a device of FIG. 1 or 2.

FIG. 5 is a schematic of a setup used for FTIR measurements on the fabricated samples. For our setup, the samples are illuminated with an IR beam from the bottom. The source may be either incoherent or coherent. As a proof of concept, we have compared the spectra of A431 (skin cancer) cells grown on vertical nanopillars topped with gold nano-antennas (3D nano-antennas: see FIG. 6) with those grown on gold nano-antennas fabricated on flat substrates (i.e. lacking the silica nanopillars: 2D nano-antennas).

Figure 6:
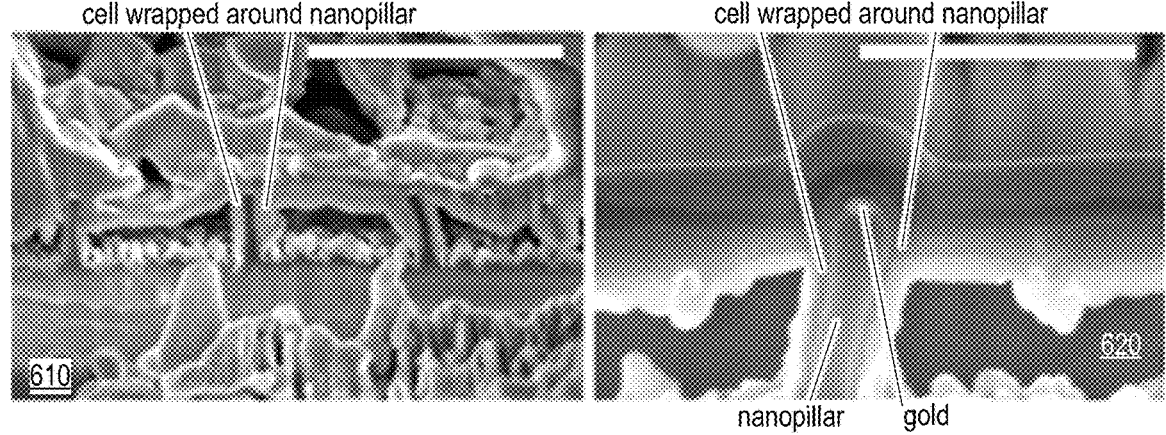
FIG. 6 includes cross-sectional images showing A431 cells wrapping around fabricated nanopillars.

FIG. 6 shows the cross-sectional images 610 and 620 of A431 cells grown on the 3D nano-antennas (3D-NA); the cells are fixed and dried prior to their sectioning. The pillar height is 850 nm. The scale bar of image 610 is 4-μm long. Image 620 is a zoomed-in region of image 610, its scale bar being 1-μm long. In image 620, the cells tightly wrap around the 3D-NAs and descend into the trenches between the nanopillars. Intimate contact between the cells and the 3D-NAs ensures that the reflection spectra contain spectral features of the cells that are more distinctive than in the case of 2D nano-antennas (2D-NAs).

Figures 7, 8:
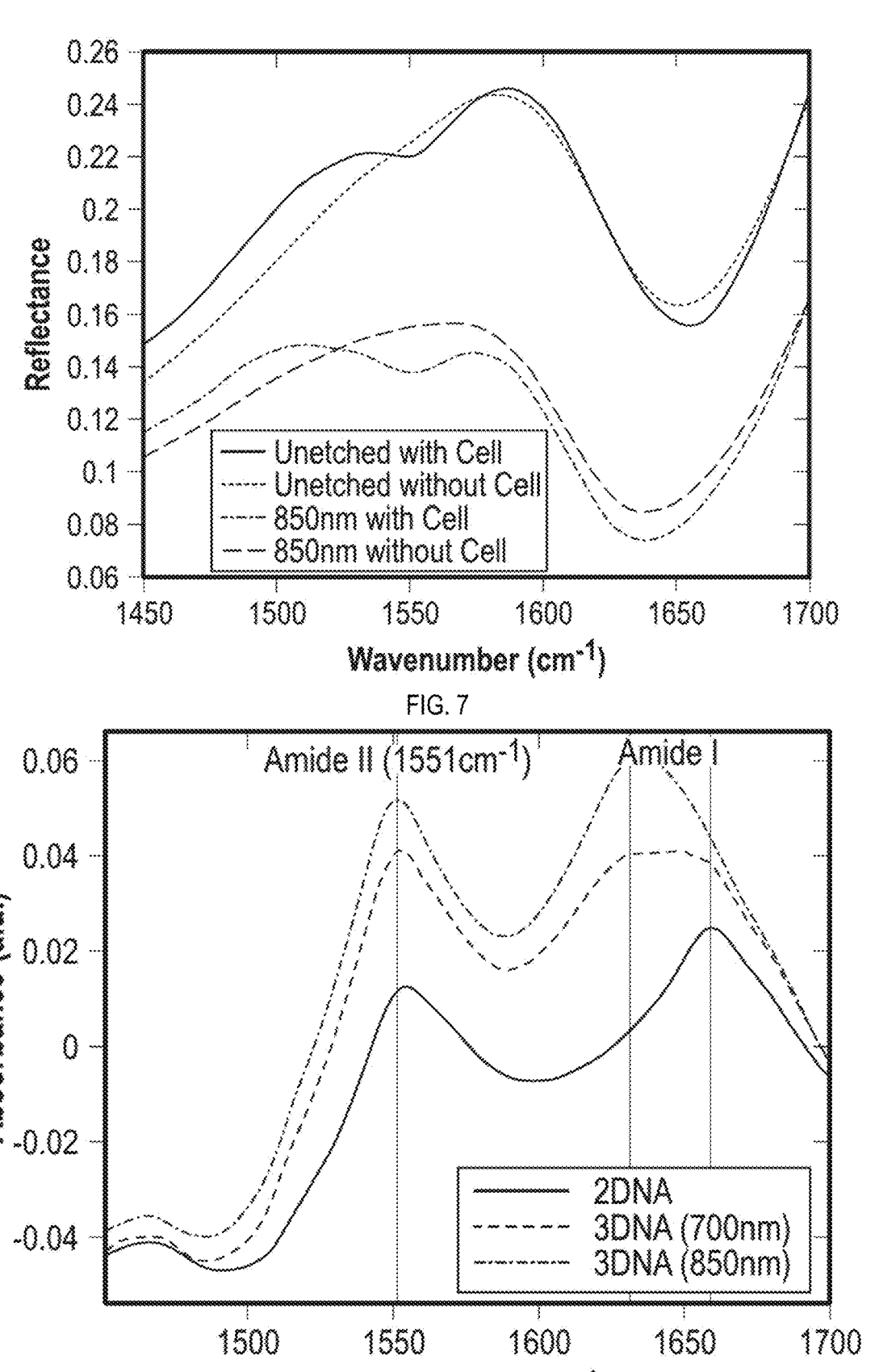
FIG. 7 is a graph of reflectance spectra measured for the nanostructures in cell medium with (without) A431 cells grown on them.
FIG. 8 is a graph of cell absorbance for A431 cells grown on two-dimensional nano-antennas (2D-NAs) and three-dimensional nano-antennas (3D-NAs).

These conclusions are confirmed by our experimental results plotted in FIG. 7 that shows the reflectance spectra obtained from A431 cells grown on 2D-NAs and 850-nm tall
3D-NAs. In a direction perpendicular to the antenna's peri-
odicity, the antenna length is 1.8 μm. A broad baseline in
reflectance corresponds to the plasmonic nano-antennas'
resonance, while the reflectance minimum at $\omega_{H2O}\approx1,650$
$cm^{-1}$ corresponds to water absorption. The presence of cells
near the 3D-NAs or 2D-NAs manifests as small dips around
$\omega_{AII}\approx1,550$ $cm^{-1}$. The ratios of the reflectance spectra with
and without the cells—referred to as the cellular absorbance
spectra A(ω) defined as $A(\omega)=-\log_{10}(R^{(cell)}(\omega)/R^{(bare)}(\omega))$,
where $R^{(cell)}(\omega)$ and $R^{(bare)}(\omega)$ are the reflection spectra
from the antenna arrays with and without cells, respec-
tively—provide a more intuitive representation of the cel-
lular vibrational spectra on the arrays of 2D-NAs and
3D-NAs.

The absorbance spectra A(ω) are plotted in FIG. 8 for one
2D-NA and two 3D-NAs, the latter ones based on two types
of nanopillars: 700-nm and 850-nm tall. For the Amide II
peak we observe an increase in the absorbance signal by the
total enhancement factors of η=1.6 (η=1.8) for the 700 nm
(850 nm) tall 3D-NAs as compared with their 2D-NA
counterparts.

The origin of this enhancement factor η>1 is two-fold.
First, we expect stronger overlap of the cytoskeleton with
3D-NAs than with 2D-NAs. Therefore, we refer to this
enhancement mechanism as the "overlap enhancement."
Second, we expect that the mid-IR light reflected from
3D-NA is going to pass through the portion of the cell
located between the pillars. We refer to this enhancement
mechanism as the "transflection enhancement." Note that
transflection enhancement does not occur for 2D-NAs
because there is essentially no cellular material between the
nano-antennas, as those are not elevated on nanopillars.

In addition to the differences in the Amide II cell absor-
bances between 2D-NAs and 3D-NAs, we also observe a
clear difference in the Amide I region for 2D vs 3D nano-
antennas. The Amide I absorbance peak appears to be
broadened for the nanopillar structures when compared to
the 2D case. It is also evident from FIG. 8 that the Amide I
peak is red-shifted for the 3D-NA substrates, especially for
the tallest one. To get a clearer image of the Amide I sub
peaks, we found it useful to take the second derivative A"
$(\omega)=d^2A/d\omega^2$ of the differential absorbance A(ω) plotted in
FIG. 8.

Figure 9:
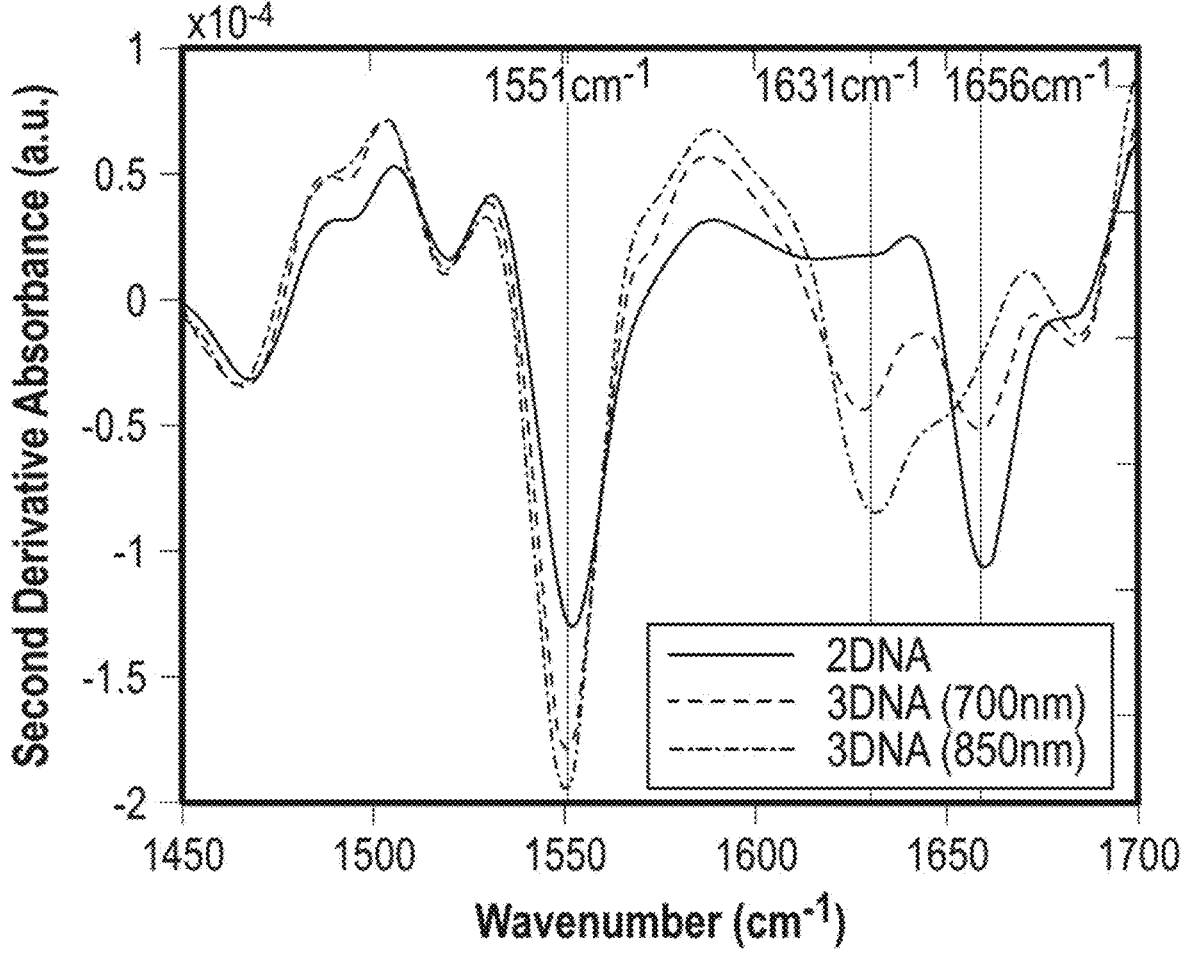
FIG. 9 is a graph of second-derivative spectra obtained from the cellular absorbance of FIG. 8.

FIG. 9 is a graph of second-derivative spectra A"(ω)
obtained from the cellular absorbance A(ω) of FIG. 8, for the
cases of 2D-NA and two 3D-NAs (d=700, 800 nm). The plot
of A"(ω) in FIG. 9 exhibits two Amide I sub-peaks $$(\omega_{A-I}^{\beta} \approx 1631 \text{ cm}^{-1} \text{ and } \omega_{A-I}^{\alpha} \approx 1656 \text{ cm}^{-1})$$

for the 3D-NAs (700 nm and 850 nm-tall), compared to the
single $$\omega_{A-I}^{\alpha} \text{ peak } (1656 \text{ cm}^{-1})$$

in the case of the 2D-NA.

Therefore, our spectroscopic measurements enhanced by
3D-NAs appear to be resolving the secondary protein struc-
ture by discriminating between β-sheets (manifested by the $$\omega_{A-I}^{\beta}$$

vibrational sub-peak) and α-helixes (manifested by the $$\omega_{A-I}^{\alpha}$$

vibrational sub-peak). We speculate that the $$\omega_{A-I}^{\beta}$$

vibrational line associated with β-sheets emerges because of
the response of the attaching cells to surfaces with varying
nanoscale topography. Specifically, we speculate that
3D-NAs induce clathrin mediated endocytosis (CME),
resulting in the translocation of β-sheets-rich adaptor pro-
teins (e.g., AP-2) to the plasma membrane, where the
secondary structure of such CME-mediating proteins is
spectroscopically detected.

1.3 Implementation: Elevated Plasmonic Nano-Gratings

The grating-on-nanopillars device illustrated in FIG. 2 has
a somewhat different working principle than the 3D-NA
device. The incident beam after travelling the height d of the
nano-grating (marked in FIG. 1) gets mostly reflected from
the grating in the case when the electric field polarization of
the incident light is parallel to the direction of the grating. To
gain insights into the functioning of the device, we con-
ducted simulations to examine the dependence of absor-
bance on height d. Specifically, we analyzed the variation in
the intensity of the water absorption line at $\omega_{H2O}\approx1,650$
$cm^{-1}$ as we systematically increased the height of the nano-
gratings.

Figure 10:
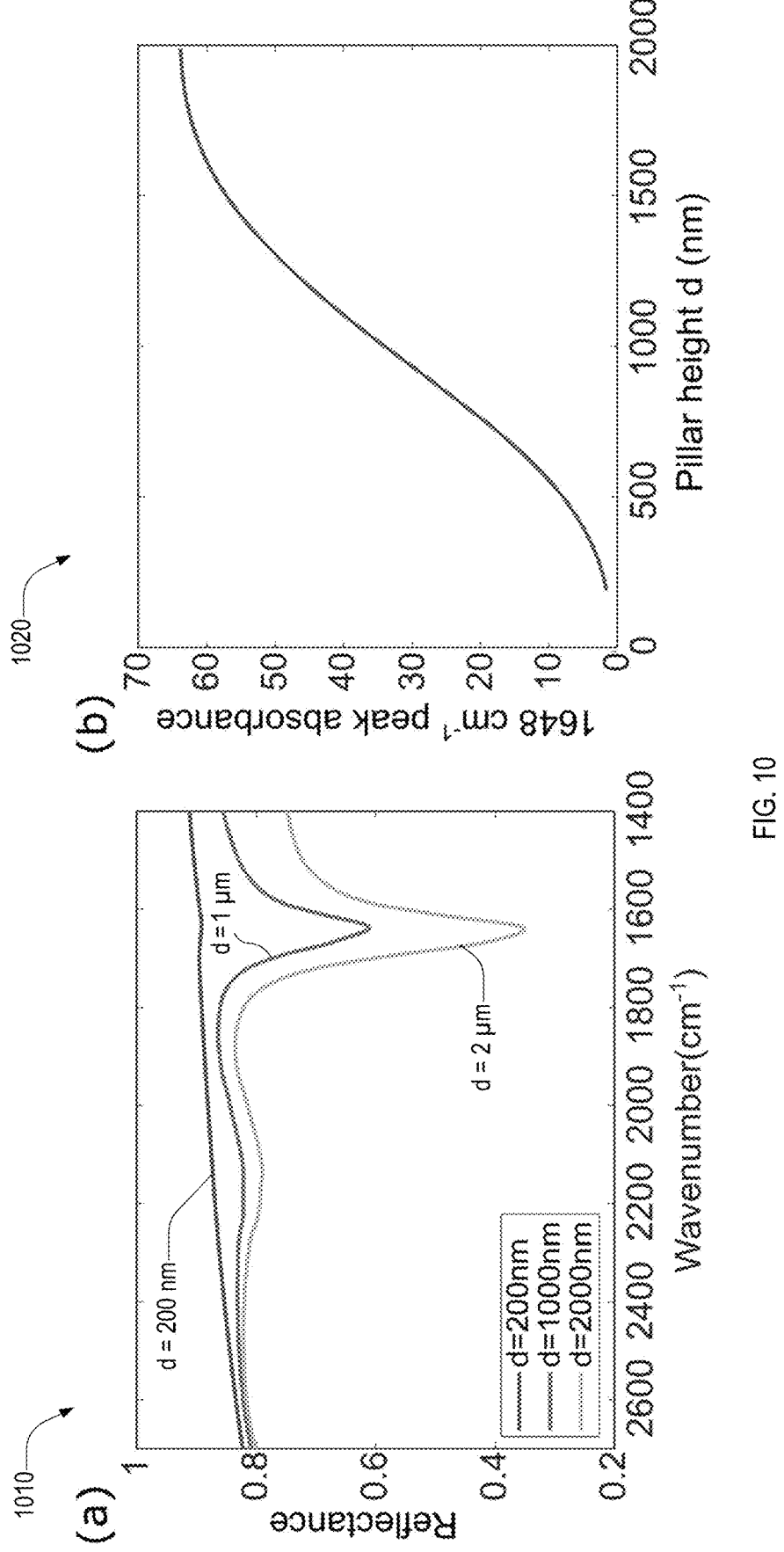
FIG. 10 is simulated spectra and peak absorbance of three-dimensional nano-gratings (3D-NGs) for three pillar heights.

FIG. 10 includes a graph 1010 of typical reflectance
spectra for the device with three different pillar heights
d=200 nm, 1000 nm and 2000 nm, with the water absorption
line prominently visible. Variation of water absorbance at
$\omega_{H2O}\approx1,650$ $cm^{-1}$, as seen from the 3D-NG spectra for pillar
heights 200 nm<d<2000 nm. Grating period: P=0.68 μm and
grating width=200 nm. Reflection of light from the grating
causes an electric field standing wave (EFSW) to be formed
in the analyte (here water) layer. This EFSW effect causes
absorbance to change non-linearly with respect to nano-
grating height. This is visible in a graph 1020 of FIG. 10,
which shows the variation of the reflectance dip intensity of
the water absorption line with height.

Next, to demonstrate that the 3D-NG device may be used
as an effective tool to study live cells, we seed and grow
A431 cells on the fabricated samples and perform FTIR
measurements on them. The measured differential absor-
bance, for varying periodicity P, due to transflection of
incident light through the cellular material in between the
nanopillars, is shown in FIG. 11.

Figure 11:
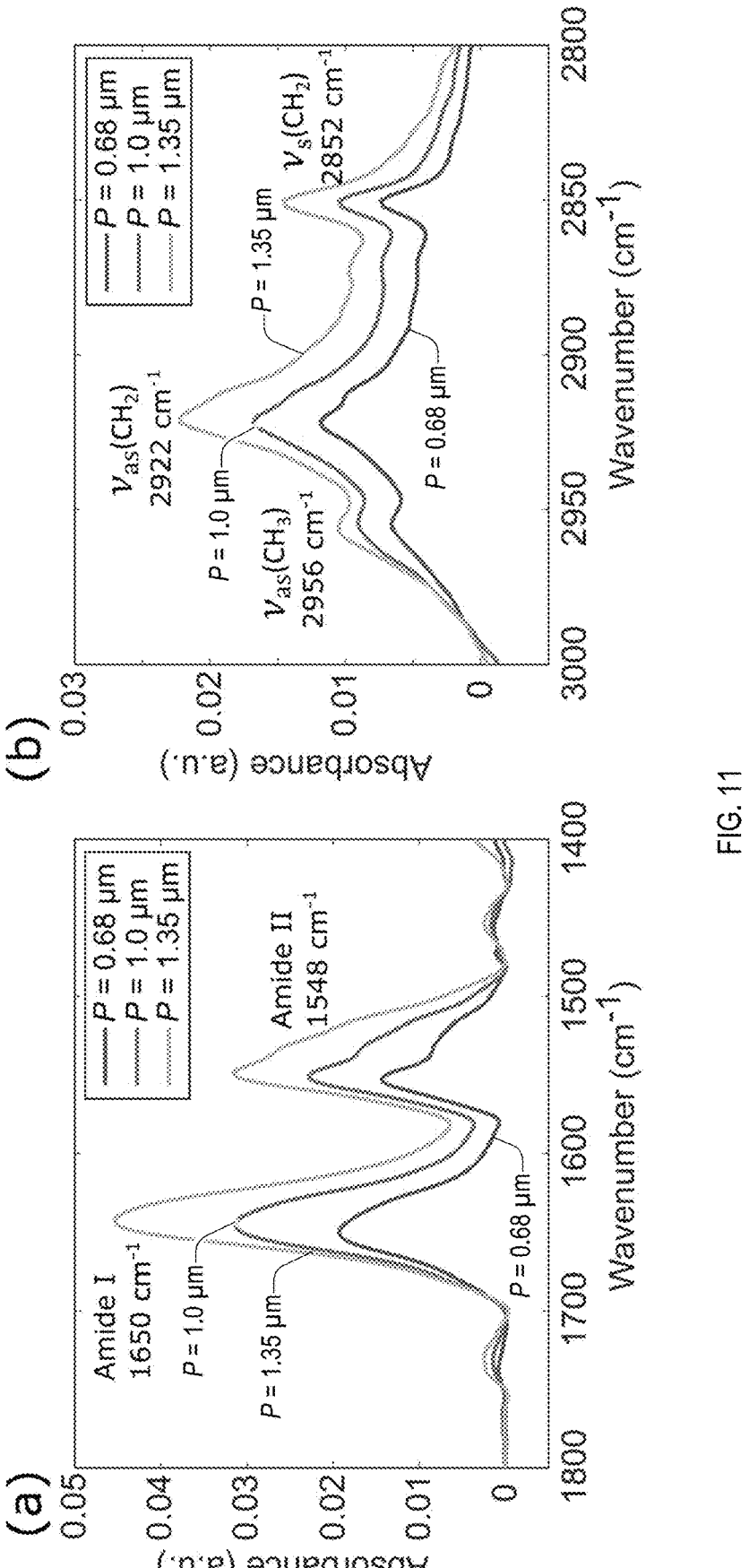
FIG. 11 includes cellular absorbance spectra measured using 3D-NG devices with different periodicities.

FIG. 11 includes cellular absorbance spectra A(ω) mea-
sured using 3D-NG devices with different periodicities:
P=0.68 μm, 1.0 μm and 1.35 μm. (Left) Spectra showing
proteins (Amide I and II); (Right) spectra showing lipids
(CH₂/CH₃). Grating height d=830 nm and width=200 nm.

The amide and lipid IR-active peaks are clearly visible.
Spectral measurements for 3 different grating periodicities
are shown: P=0.68 μm, 1.0 μm and 1.35 μm. Grating width
at 200 nm is maintained the same for all the periodicities. As
evident from FIG. 11, increasing the periodicity increases
the measured signal. This arises because of the increase in
cellular material between adjacent gratings with increasing
periodicity.

Figure 12:
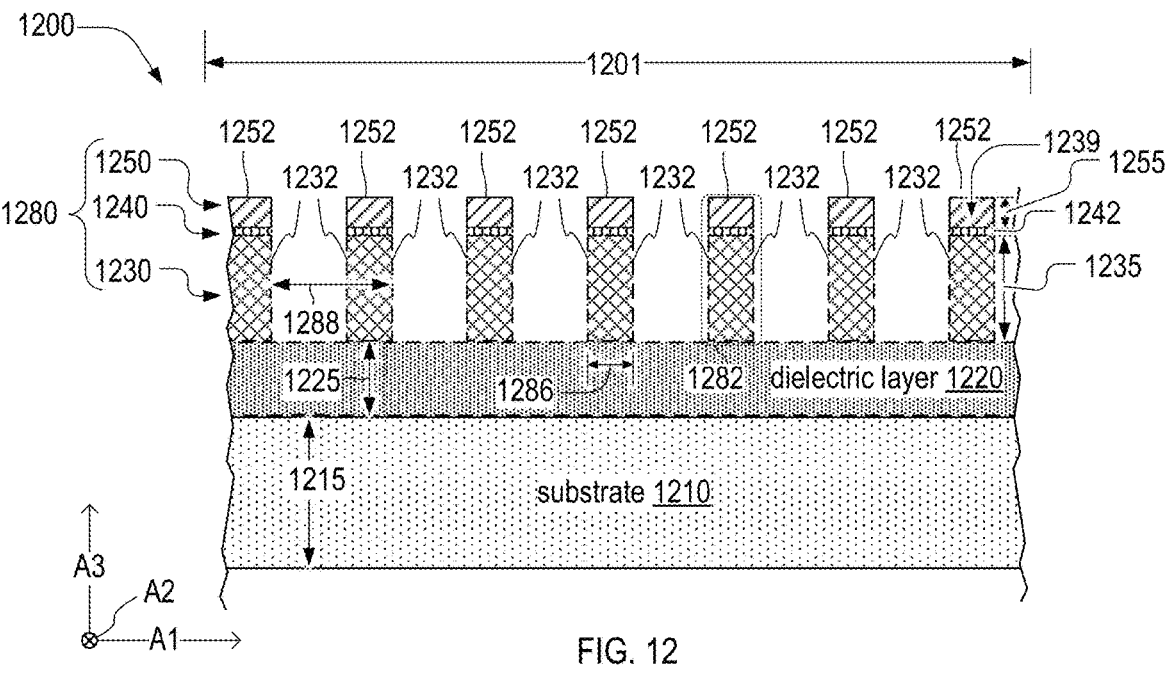
FIG. 12 is a cross-sectional view of a plasmonic nano-structure, in an embodiment.

FIG. 12 is a cross-sectional view of a plasmonic nano-structure 1200, embodiments of which include plasmonic nano-antennae and plasmonic nano-gratings, each of which may be elevated or non-elevated. Plasmonic nanostructure 1200 includes a substrate 1210 and a conductive-layer array 1250 on substrate 1210. Plasmonic nanostructure 1200 may also include at least one of a pillar-array 1230 and a dielectric layer 1220 between substrate 1210 and conductive-layer array 1250. When plasmonic nanostructure 1200 includes pillar-array 1230, pillar-array 1230 is between conductive-layer array 1250 and substrate 1210.

Plasmonic nanostructure 1200 may also include an adhesion-layer array 1240 between conductive-layer array 1250 and at a layer directly beneath conductive-layer array 1250. This layer may be one of substrate 1210, dielectric layer 1220, and pillar-array 1230.

Figures herein depict axes A1, A2, and A3. Unless otherwise specified, heights and depths of objects herein refer to the object's extent along axis A3. Also, herein, a horizontal plane is parallel to the A1-A2 plane, a width refers to an object's extent along axis A1 or axis A2, and a vertical direction is along axis A3. Axis A3 may be orthogonal to the A1-A2 plane. Axes A1 and A2 may be orthogonal or non-orthogonal.

Plasmonic nanostructure 1200 may be designed to function as an operating wavelength or range of operating wavelengths. The operating wavelength may be an IR wavelength, e.g., a wavelength between 0.7 μm and 100 μm, for example, between one micrometer and twenty micrometers. In some embodiments, the operating light wavelength is associated with a resonance wavelength of the nanostructure in its ambient environment, examples of which include water, solvent, cells, or a medium. Along axis A1, plasmonic nanostructure 1200 has a width 1201, which may be 0.1 millimeters and five millimeters. For example, width 1201 may be between 0.2 millimeters and 0.4 millimeters.

Conductive-layer array 1250 includes a periodic array of conductive layers 1252. In embodiments, conductive layer 1252 does not completely cover pillar-array 1230 such that biological cells can penetrate into a region below conductive layer 1252, which may enhance signal strength. For example, a conductive layer 1252 may include a plurality of holes into which biological cells can penetrate. The plurality of holes may be arranged as a periodic array (such that layer 1252 is or includes a metallic mesh), or as a non-periodic distribution in a horizontal cross-section. The plurality of holes may include one or both of through holes and blind holes. The hole dimensions in the horizontal plane may be between 100 nm and ten micrometers while also being less than width 1286 along axis A1 and a maximum dimension of pillar 1232 along axis A2.

Pillar-array 1230 includes a periodic array of dielectric pillars 1232. When plasmonic nanostructure 1200 includes pillar-array 1230, each conductive layer 1252 is on a respective dielectric pillar 1232, such that each dielectric pillar 1232 is between a respective conductive layer 1252 and substrate 1210. Each conductive layer 1252 is on, e.g., directly on, a top pillar-surface 1239 of a respective dielectric pillar 1232. Adhesion-layer array 1240 includes a periodic array of adhesion layers 1242, each of which is between a respective pillar 1232 and a conductive layer 1252.

FIG. 12 denotes a multi-layer pillar 1282, which includes one conductive layer 1252 and may also include one or both of one pillar 1232 and one adhesion layer 1242. Multi-layer pillar 1282 has a width 1286 along axis A1. Width 1286 affects both the optical resonance and the interaction of plasmonic nanostructure 1200 with biological cells thereon.

Width 1286 may be a width of both a pillar 1232 and conductive layer 1252. Width 1286 may be greater than or equal to fifty nanometers and may be less than or equal to 0.5 micrometers. Plasmonic nanostructure 1200 includes a periodic array of multi-layer pillars 1282, which together form an array 1280. Array 1280 therefore includes conductive-layer array 1250 and may also include at least one of pillar-array 1230 and adhesion-layer array 1240.

Array 1280 may be a periodic array or non-periodic array along axis A1 and has a spacing 1288 between adjacent multi-layer pillars 1282. When array 1280 is a non-periodic array, spacing 1288 is not uniform between adjacent pillars 1282. The operating wavelength λ of plasmonic nanostructure 1200 may be greater than 2 nΛ, where Λ is spacing 1288 and n is the refractive index of the ambient medium of plasmonic nanostructure 1200, e.g., between and above pillars 1282. Spacing 1288 may be within one or more of the following ranges: 0.5-20 micrometers, 1-5 micrometers, 2-4 micrometers, 0.3-2 micrometers, and 0.5-1 micrometer. In embodiments, spacing 1288 may be between $\lambda/(2n)$ and $\lambda/n$.

When array 1280 is a one-dimensional array (e.g., along axis A1 only), array 1280 may function as a diffraction grating at certain wavelengths. Array 1280 may be a two-dimensional array, as in plasmonic nano-antenna 1400, FIG. 14, described below.

When plasmonic nanostructure 1200 does not include dielectric layer 1220, pillar-array 1230 may be directly on a top surface of substrate 1210. When plasmonic nanostructure 1200 does not include pillar-array 1230, conductive-layer array 1250 may be either directly on either substrate 1210 or, when plasmonic nanostructure 1200 includes dielectric layer 1220, directly on dielectric layer 1220.

Substrate 1210 may be dielectric substrate and/or may have a material composition that includes a dielectric. The material composition may include one of calcium fluoride, silicon, silica, germanium, barium fluoride, zinc selenide, and zinc sulfide, or any combination thereof. Each adhesion layer 1242 may have a material composition that includes one of chromium, titanium, or a combination thereof. Each conductive layer 1252 may have a material composition that includes one of gold, silver, platinum, copper, aluminum, chromium, titanium, indium tin oxide, and graphene, or any combination thereof.

Each of dielectric layer 1220 and pillars 1232 may have a material composition that includes one of silica, aluminum oxide, aluminum nitride, silicon nitride, titanium dioxide, silicon, germanium, diamond, calcium fluoride, zinc selenide, and zinc sulfide, or any combination thereof. In embodiments, dielectric layer 1220 and pillars 1232 have the different material compositions. In embodiments, dielectric layer 1220 and pillars 1232 have the same material composition. For example, dielectric layer 1220 and pillars 1232 may be monolithic. Each pillar 1232 may be a protrusion of dielectric layer 1220 extending away from substrate 1210 such that (a) a top pillar-surface 1239 of each dielectric pillar 1232 is a respective region of a top surface of the dielectric layer 1220.

In embodiments, substrate 1210 is optically transparent in the operating wavelength and/or operating wavelength range. In other embodiments, substrate 1210 has a transmission between 10% and 100% including any number therein and any subranges therebetween (e.g., greater than or equal to 20%, 30%, 40%, 50%, 60%, 70%, or 80%) in the operation light wavelength ranges.

Substrate 1210, dielectric layer 1220, pillar-array 1230, and conductive-layer array 1250 have respective thicknesses 1215, 1225, 1235, and 1255. Thickness 1215 may be between ten micrometers and ten millimeters. For example, thickness 1215 may be between 100 micrometers and 2 mm. Thickness 1225 may be between zero and 100 micrometers. When thickness 1225 equals zero, plasmonic nanostructure 1200 does not includes dielectric layer 1220. For example, 1225 may be between five nanometer and two micrometers.

When thickness 1235 is too small, there is insufficient path length for optical absorption. When thickness 1235 is too large, there is too much attenuation from optical absorption by water. Thickness 1235 may be less than twenty micrometers. For example, thicknesses 1235 may be between 0.2 micrometers and two micrometers. Thickness 1255 may be between one nanometer and one micrometer. For example, thickness 1255 may be between 10 nm and 100 nm or between fifty nanometers and one hundred micrometers.

Figure 13:
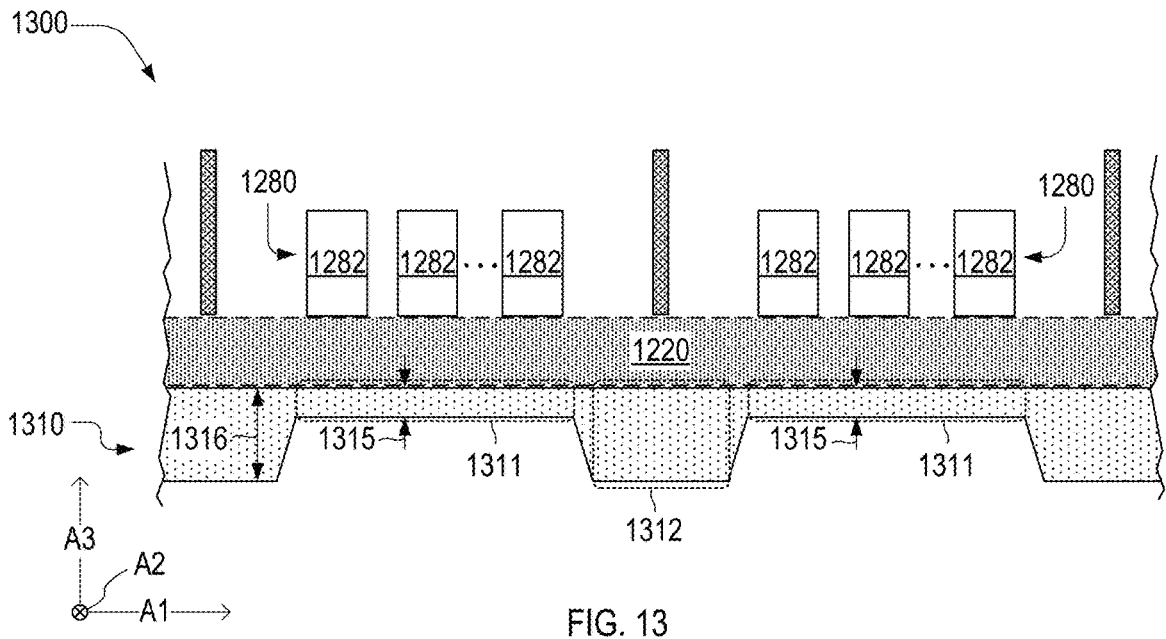
FIG. 13 is a cross-sectional view of a plasmonic nano-structure, which is an example of the plasmonic nanostructure of FIG. 12.

FIG. 13 is a cross-sectional view of a plasmonic nanostructure 1300, which is an example of plasmonic nanostructure 1200. The plasmonic nanostructure of FIG. 3 is an example of plasmonic nanostructure 1300.

Plasmonic nanostructure 1300 includes a substrate 1310, a dielectric layer 1220, and array 1280. Plasmonic nanostructure 1300 may include additional arrays 1280, as shown in FIG. 12. Substrate 1310 is an example of substrate 1210.

Substrate 1310 includes a central substrate-region 1311 beneath each array 1280 and a peripheral substrate-region 1312 surrounding central substrate-region 1311. Regions 1311 and 1312 have respective thicknesses 1315 and 1316, where thickness 1316 exceeds thickness 1315. In embodiments thickness 1315 equals zero such that each central substrate-region 1311 is an aperture of substrate 1310 that is surrounded by a respective peripherical substrate-region 1312. The air-bridged membrane of FIG. 3 is an example of substrate 1310 when thickness 1315 equals zero.

Figure 14:
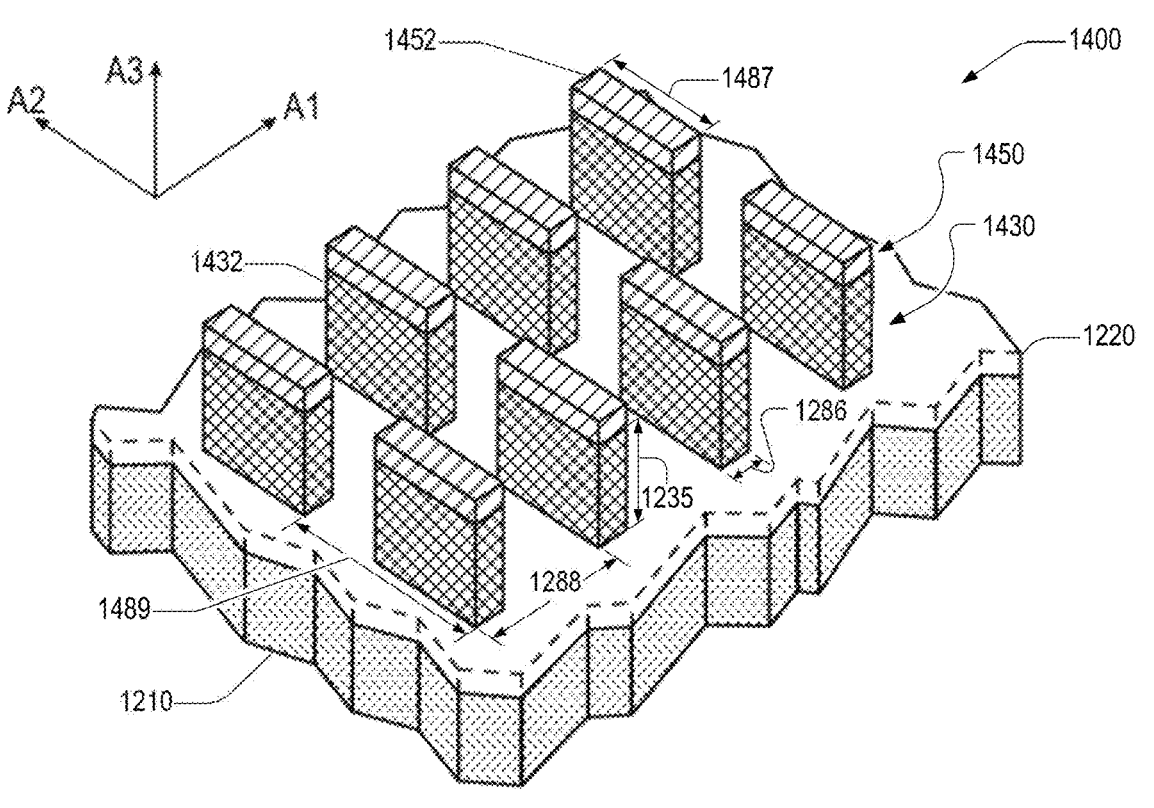
FIGS. 14-16 are isometric views of a respective plasmonic nanostructure, each of which is an example of the plasmonic nanostructure of FIG. 12.
Figure 15:
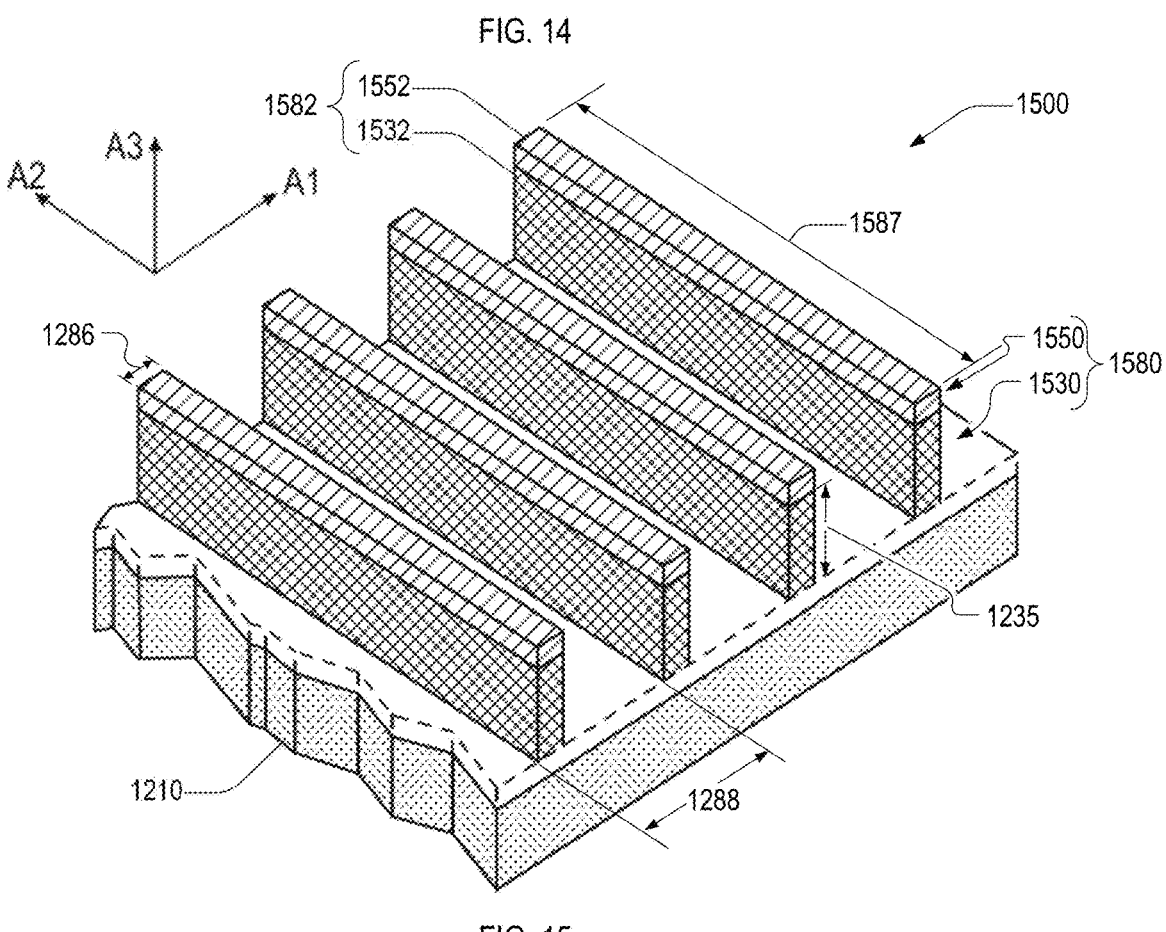
Figure 16:
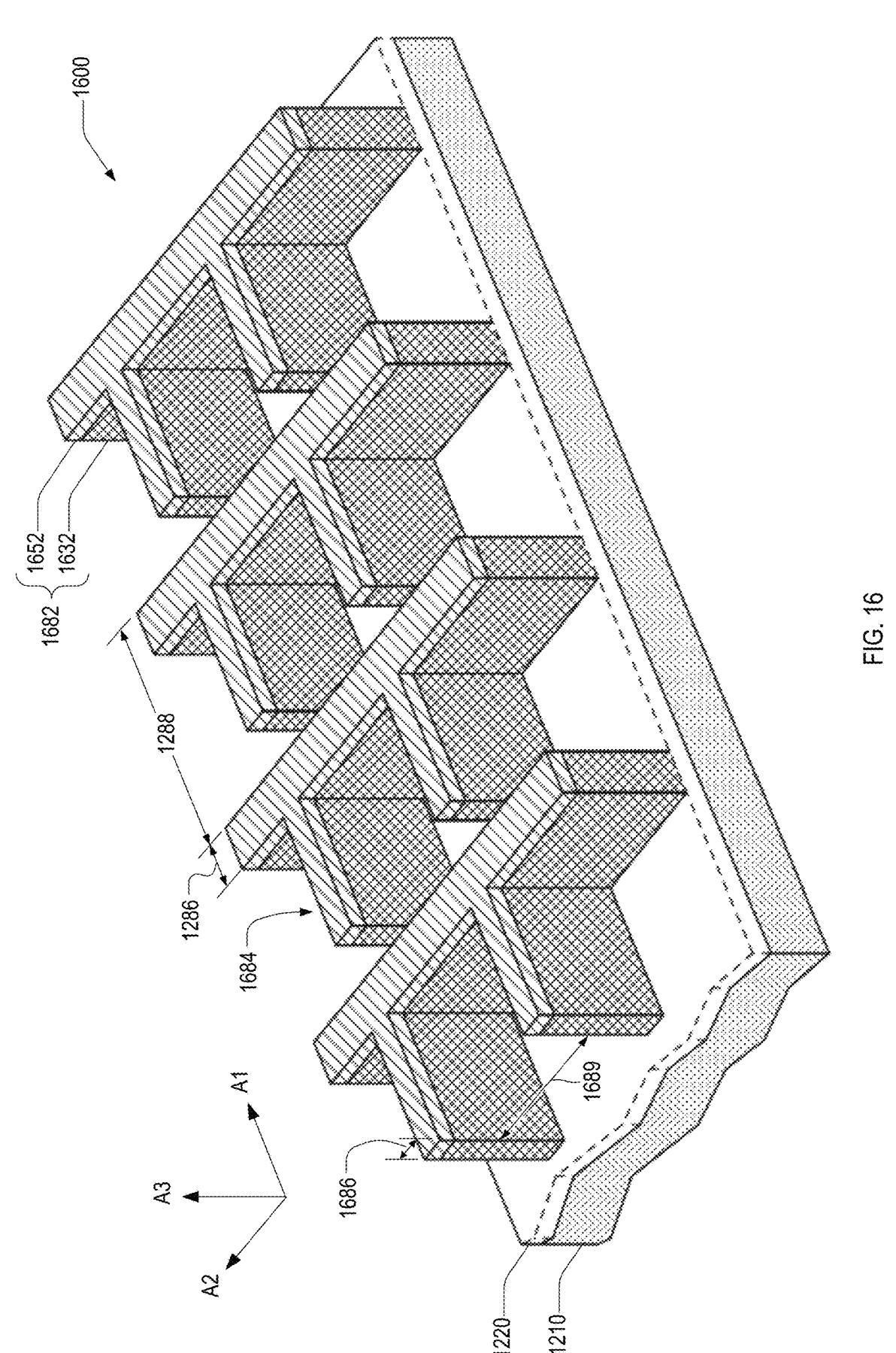

FIGS. 14-16 are isometric views of a plasmonic nano-antenna 1400, a plasmonic nano-grating 1500, and a plasmonic nanostructure 1600, respectively, each of which has the cross-sectional view of FIG. 12 in a vertical plane parallel to the A1-A3 plane. The plasmonic nanostructure of FIGS. 1 and 2 are examples of plasmonic nano-antenna 1400 and plasmonic nano-grating 1500, respectively.

Plasmonic nano-antenna 1400 includes substrate 1210 and a conductive-layer array 1450 on substrate 1210. Plasmonic nanostructure 1200 may also include at least one of a pillar-array 1430, dielectric layer 1220, and adhesion-layer array 1240.

Pillar-array 1430 includes a plurality of dielectric pillars 1432. Conductive-layer array 1450 includes a plurality of conductive layers 1452. Pillar-array 1430, conductive-layer array 1450, plurality of dielectric pillars 1432, and plurality of conductive layers 1452, are respective examples of pillar-array 1230, conductive-layer array 1250, pillars 1232, and conductive layer 1252 of plasmonic nanostructure 1200.

Each of pillar-array 1430 and conductive-layer array 1450 is a two-dimensional periodic array having spacing 1288 along axis A1 and a period 1489 along axis A2. Each dielectric pillar 1432 has width 1286 along axis A1 and a length 1487 along axis A2. Length 1487 is less than period 1489. Length 1487 may be between 0.4 micrometers and 7 micrometers, for example, in the range of 1.2-1.4 micrometers. In embodiments, length 1487 equals or exceeds width 1286. For example, a ratio of length 1487 to width 1286 may be between three and thirty-five.

The value of length 1487 depends on the vibrational band of interest. For example, length 1487 may be between 1.7 and 1.8 micrometers, which enables excitation of protein absorption bands at Amide I (around 1650 cm$^{-1}$) and Amide II (around 1550 cm$^{-1}$).

Period 1489 may be between 0.5 micrometers and 20 micrometers. For example, period 1489 may be within a smaller range, examples of which include between one micrometer and five micrometers and between two micrometers and four micrometers. While FIG. 14 illustrates a conductive-layer array 1450 as a rectangular array, conductive-layer array 1450 may be a non-rectangular two-dimensional array, e.g., hexagonal, without departing from the scope hereof.

FIG. 15 is an isometric view of a plasmonic nano-grating 1500, which is an example of plasmonic nanostructure 1200. The plasmonic nanostructure of FIG. 2 is an example of plasmonic nano-grating 1500.

Plasmonic nano-grating 1500 includes substrate 1210 and a conductive-layer array 1550 on substrate 1210. Plasmonic nanostructure 1200 may also include at least one of a pillar-array 1530, dielectric layer 1220, and adhesion-layer array 1240. In embodiments, plasmonic nano-grating 1500 is periodic only along axis A1, such that each of pillar-array 1530 and conductive-layer array 1550 is a one-dimensional array.

Pillar-array 1530 includes a plurality of dielectric nanoridges 1532. Conductive-layer array 1550 includes a plurality of conductive layers 1552. Pillar-array 1530, conductive-layer array 1550, plurality of dielectric nanoridges 1532, and plurality of conductive layers 1552, are respective examples of pillar-array 1230, conductive-layer array 1250, pillars 1232, and conductive layer 1252 of plasmonic nanostructure 1200. Each of pillar-array 1530 and conductive-layer array 1550 is periodic along axis A1 and has a length 1587 along axis A2. Length 1587 may be between 0.1 millimeters and five millimeters. For example, length 1587 may be between 0.2 millimeters and 0.4 millimeters. A ratio of length 1587 to width 1286 may be between one hundred and 10$^5$.

Dielectric pillars 1432, nanoridges 1532, and conductive layers 1452 and 1552 may have polygonal cross-sections in horizontal planes, for example, a rectangular cross-section as shown in FIGS. 14 and 15. The polygonal cross-section may be non-rectangular, e.g., that of a polygon with at least four sides, such as a pentagon or a hexagon, without departing from the scope hereof.

FIG. 15 denotes an array 1580, which includes conductive-layer array 1550 and may also include at least one of pillar-array 1530 and adhesion-layer array 1240. Array 1580 includes a plurality of multi-layer pillars 1582, each of which is an example of multi-layer pillar 1282. Each multi-layer pillar 1582 includes a conductive layer 1552 and may also include at least one dielectric nanoridge 1532 and an adhesion layer 1242.

FIG. 16 is a cross-sectional view of a plasmonic nanostructure 1600, which is an example of plasmonic nanostructure 1200. Plasmonic nanostructure 1600 functions as a nano-antenna with A1-polarized light, and as a nano-grating with A2-polarized light.

Plasmonic nanostructure 1600 includes a plurality of plurality of multi-layer protrusions 1682 that form an array 1680, which are respective examples of plurality of multi-layer pillars 1582 and array 1580. Array 1680 is periodic along axis A1. Each multi-layer protrusion 1682 includes at least one protrusion 1684 extending along axis A1. Along axis A1, the length of protrusion 1684 is less than spacing 1288 of array 1580. Protrusion 1684 has a width 1686 along axis A2. Width 1686 may be within aforementioned ranges of width 1286. In plasmonic nanostructure 1600, width 1686 may be greater than, equal to, or less than width 1286.

When each multi-layer protrusion 1682 has just one protrusion, its cross-section in a horizontal plane is T-shaped. When each multi-layer protrusion 1682 includes two protrusions, one protrusion, its cross-section in a horizontal plane may be double-T shaped, resembling a cross-section of double-T beam load-bearing structure. Adjacent protrusions 1682 are spaced by a spacing 1689 along axis A2. In embodiments, spacing 1689 may be between $\lambda/(2n)$ and $\lambda/n$.

1.4 Additional Nanostructure Embodiments

In some embodiments, the plurality of pillars and/or antennas are elongated elements arranged as gratings. In some embodiments, a first distance between two adjacent pillars, antennas, or gratings is associated with $\lambda/2n$ or designed by $\lambda/2n$, wherein $\lambda$ is the wavelength of the operation light in vacuum and n is an effective refractive index of the operating environment (e.g., water, air, a solvent, cells, or a medium). In some embodiments, the first distance is about $\lambda/n$ or less, including any values therein and any subranges therebetween. In some embodiments, the first distance is between $0.1\lambda/n$ and $10\lambda/n$, including any values therein and any subranges therebetween, e.g., $0.5\lambda/n$–$3\lambda/n$. In some embodiments, the first distance is less than A/n such that the operation light with a first polarization parallel to the grating lines traveling toward the gratings gets reflected from the gratings and, in embodiments, a second polarization (e.g. the orthogonal light polarization of the first polarization) is transmitted with minimal reflection. In some embodiments, the reflection of the first polarization by the gratings is between 10% and 100% including any percentage therein and any subranges therebetween for the first polarization, e.g., 80%-100%. In embodiments, the reflection of the second polarization by the gratings is between 0% and 50% including any percentage therein and any subranges therebetween for the first polarization, e.g., 0% to 30%.

In some embodiments, the plurality of pillars and/or antennas form a two-dimensional array in the A1-A2 plane. The first distance is along a first axis (e.g., axis A1) and a second distance between adjacent pillars or gratings is along axis A1. The second distance may be substantially the same as the first distance. In other embodiments, the second distance between adjacent pillars, antenna, or gratings is different from the first distance (e.g., greater than the first distance or less than the first distance). In some embodiments, the second distance is substantially the same as or less than the first distance. In other embodiments, the second distance is greater than the first distance. In some embodiments, a plurality of pillars and/or antennas are elongated along a dimension of the operation region of the plasmonic optical structure such that there is only a first distance between two adjacent pillars/antennas. In some embodiments, the gratings have a substantially uniform first distance, a substantially uniform second distance, or both. In other embodiments, the gratings are not periodic and have nonuniform distance(s), but the spacing or the nonuniform distance(s) between adjacent gratings are less than $\lambda/n$ or substantially equal to $\lambda/n$.

In some embodiments, each of the pillars, antenna, or gratings in at least part of the array of the plasmonic optical structure has a rectangular shape or an elongated shape with a width and a length from a top view, wherein the width is less than the length. In some embodiments, the length is within a range of 0.1 μm to 128 mm including any value therein and any subranges therebetween, e.g., from 0.4 μm to 7 μm. In some embodiments, the width is selected from 50 nm up to the length including any value therein and any subranges therebetween, e.g., 100 nm to 300 nm. In some embodiments, the length-to-width ratio is at least 1.0, 1.1, 1.2, 1.3, 1.4, 1.5, 1.6, 1.7, 1.8, 1.9, 2, 3, 4, 5, 6, 7, 8, 9, 10, 15, 20, 25, 30, 40, 50, 60, 70, 80, 90 or 100. In some embodiments, the length-to-width ratio is within the range of 1 to 2,560,000, including any value therein and any subranges therebetween.

In some embodiments, the array of the plasmonic optical structure comprises a first portion of the pillars, antennas, or gratings in a first shape or a first structure (e.g. a rectangular shape or an elongated shape from a top view) configured to operate in a first polarization and a second portion of the pillars, antennas, or gratings in a second shape from top view or a second structure different from the first shape or the first structure in shape, orientation, or both, wherein the second portion is configured to operate in a second polarization.

In some embodiments, the array of the plasmonic optical structure has at least one dimension between 100 μm and 128,000 μm, including any value therein and any subranges therebetween, e.g., between 100 μm and 5,000 μm.

2 Imaging with Plasmonic Nanostructures

Live-cell mid-infrared (MIR) imaging has always been challenging because of the absorptive nature of water. However, there is a strong drive to image this spectroscopic window—to see the protein and lipid vibrations directly without the help of dyes. Though the dyes are convenient for imaging, they interfere with the biological functions of live cells. In the past two decades, people have relied on attenuated total reflectance (ATR) Fourier transform infrared (FTIR) spectroscopic imaging to probe such systems to reduce the infrared penetration depth to a few microns.

Plasmonic nanoantennas and nanostructures disclosed herein, which include metasurfaces, further restrict the penetration to a hundred nanometers. These structures are used for metasurface-enhanced infrared reflection spectroscopy (MEIRS), e.g., for either label-free spectroscopy or imaging. Advances in commercial mid-infrared quantum cascade lasers (QCLs), enable opportunities to acquire high-quality single-cell resolution metasurface-enhanced infrared reflection chemical imaging (MIRCI), which reveals the important protein information in real time. Herein, we disclose an inverted QCL microscope setup and cultured the cells on a cell-culture multiwell plate. The bottom of the multiwells is made of infrared-transparent window and with metasurface fabricated thereon. Herein, we disclose two proofs of concept of MIRCI on both fixed cells in water (single-cell resolution and spectroscopy) and live cells (capturing cell adhesion process). The application provides a novel tool to the drug discovery and fundamental cell biology research.

For years, most live cell imaging has been relying on labelling or high illumination. Though they provide excellent spatial resolution, the phototoxicity or dye-toxicity is non-ideal for cellular viability. Also, to know the composition of cells, a destructive measurement is usually required. Either the cells have to be fixed by formaldehyde and dried for infrared (IR) spectroscopy, or frozen for electron-microscope-based elemental analysis. Stimulated Raman scattering (SRS) or coherent anti-Stokes Raman scattering (CARS) microscopy is capable of chemically imaging the live cells without labelling, but the high optical power required for the nonlinear scattering of light is still phototoxic. IR chemical imaging, on the other hand, typically require much smaller optical power, so the phototoxicity is greatly reduced.

However, there is a persistent challenge in the IR spectroscopy of live cells: water, the fundamental of life, ironically impedes IR live cell studies as it heavily absorbs IR light. In the past two decades, people have been using attenuated total reflectance (ATR) Fourier transform infrared (FTIR) spectroscopic imaging to probe such systems to reduce the penetration depth of IR to a few microns. However, the geometric requirement of the setup makes it hard to scale up the studies.

With the recent advancement in commercial mid-infrared (MIR) quantum cascade laser (QCL), we now have the means to conduct MEIRS in a high-throughput format. That is, the inclusion of standard microwells makes it easier to work with live cells and increases the sample sizes of the experiments. With a simple adaptation to microwells (replacing the bottom with an MIR-transparent substrate and nanostructures fabricated on top of the substrate), we acquire high-quality single-cell resolution MIR chemical imaging with our customized inverted QCL microscope, which reveals the important protein information of live cells in real time.

Embodiments disclosed herein include nanostructure-enhanced infrared reflection chemical imaging (MIRCI) and single-cell MIR spectroscopy on a fixed-cell sample. We also disclose a frame of footage showing MIRCI on a simple live-cell process that suspended live cells free-fell and adhered to the nanostructure.

2.1 Inverted Microscope

Figure 17:
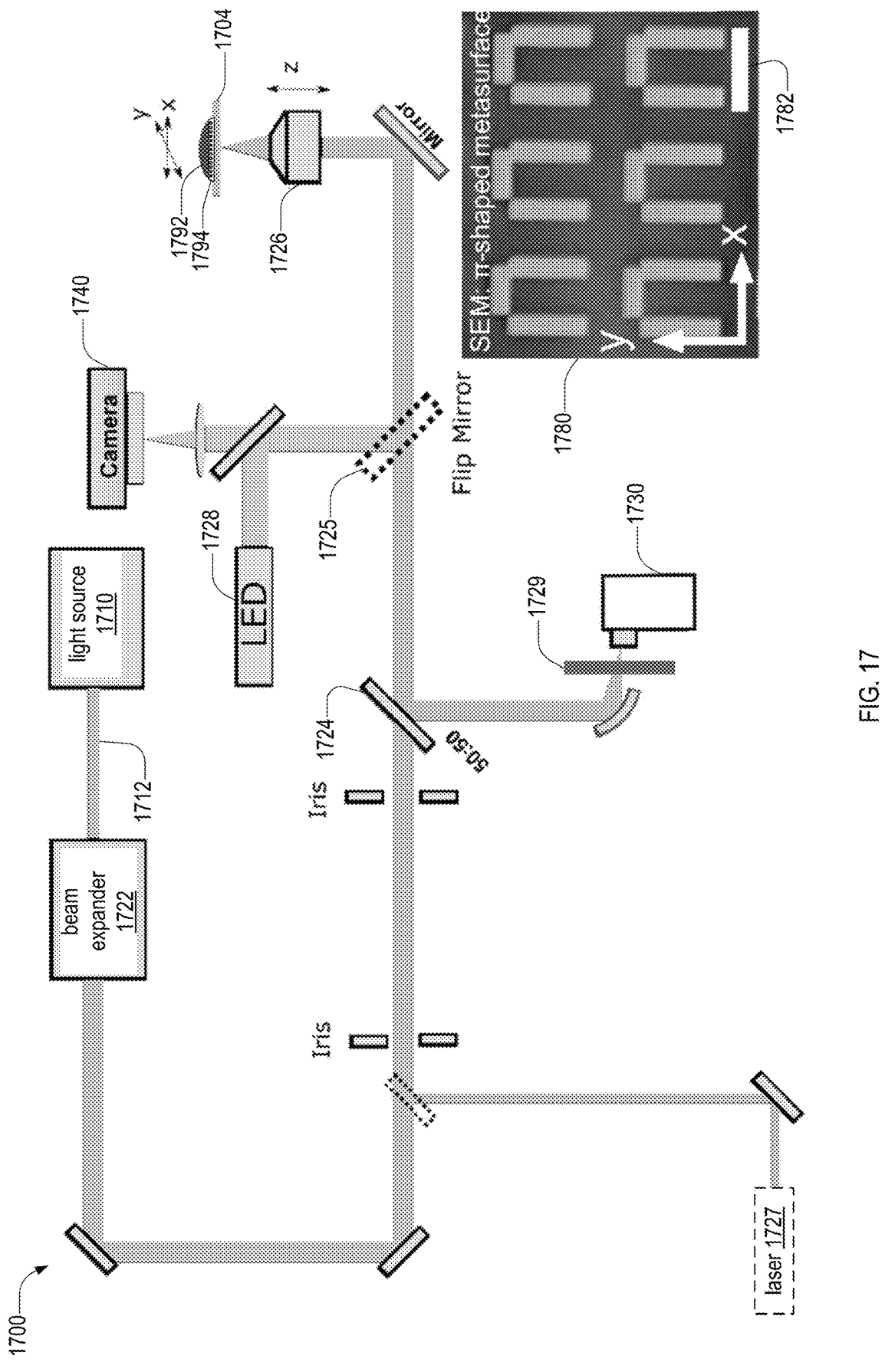
FIG. 17 is a schematic of a system that images a sample adhered to a plasmonic nanostructure of FIG. 12, in an embodiment.

FIG. 17 is a schematic of an imaging system 1700. In the use scenario of FIG. 17, imaging system 1700 is imaging a sample 1792. Sample 1792 may include live cells, and is adhered to a plasmonic nanostructure 1794, which is example of plasmonic nanostructure 1200. In embodiments, sample 1792 spans N periods of nanostructure 1794, where N is greater than or equal to one. For example, N may be an integer less than ten.

Plasmonic nanostructure 1794 may be located at the bottom of a microwell or a petri dish. An inset 1780 shows a scanning electron microscope (SEM) image of the π-shaped nanostrucure, which is an example of plasmonic nanostructure 1200. A scale bar 1782 denotes a 1-μm length.

Imaging system 1700 includes at least one of a light source 1710, a beam expander 1722, a beam splitter 1724, a flip mirror 1725, an imaging objective 1726, a visible laser 1727 for alignment, and an LED 1728, a neutral density filter 1729, a detector 1730, and a camera 1740. Light source 1710 may at least one of: include a QCL or an optical parametric amplifier, be tunable, be a mid-infrared light source, and have bandwidth less than 5 cm⁻¹. Detector 1730 may be a Fourier transform infrared spectrometer or a mercury-cadmium-telluride (MCT) detector.

Light source 1710 may emit coherent light or incoherent light. For example, light source 1710 may be a broad-band IR light source such as those used for FTIR spectroscopy. Light source 1710 produces an optical beam 1712. In embodiments a center wavelength of optical beam 1712 is between two micrometers and twenty micrometers. In certain embodiments, the center wavelength is between three micrometers and eight micrometers.

Beam splitter 1724 may be a 50/50 beam splitter, and may be formed of calcium fluoride. Imaging objective 1726 may be a reflective Cassegrain objective or a refractive objective. Camera 1740 may be a visible camera, e.g., a monochrome camera.

A customized inverted microscope is presented in FIG. 17 to accommodate the use of microwells (or petri dishes) in live or fixed cell experiments. A ZnSe focusing objective with NA=0.25, an example of imaging objective 1726, was used for both IR and visible imaging. We coarsely aligned the focus with a camera 1740, then flipped mirror 1725 to the IR light source for fine alignment. The theoretical diffraction limit d is calculated by the formula equation (1)

$$d = \lambda/2NA. \tag{1}$$

At λ=6.45 μm (i.e. 1,550 cm⁻¹, Amide II), d=12.9 μm.

In embodiments, optical beam 1712 is reflected by the live or fixed cells on the nanostructure was collected by a liquid-nitrogen-cooled mercury-cadmium-telluride (MCT) detector (an example of detector 1730) connected to a lock-in amplifier. We set light source 1710 (a QCL laser in this example) to have pulse width of 100 ns and a repetition rate of 99,009 Hz (also used as the lock-in reference). The laser power was measured to be 0.1 mW at 1=6.46 μm before entering the objective. Note that the laser power could be further reduced to 10 μW if we removed the neutral density filter (OD=1) before the MCT detector. The laser polarization was along the y-axis of the π-shaped nanoantennas (See the inset of FIG. 17).

Sample 1792 was loaded on a translation stage 1704 for point-to-point image scanning. Translation stage 1704 may be programmable and/or motorized. Mid-IR light from light source 1710 is focused by imaging objective 1726 to a diffraction limited spot. This focal spot is raster scanned across sample 1792 by moving the sample stage. The reflected light intensity at different spatial locations is collected by detector 1730 and mapped out to form the image of sample 1792. Imaging system 1700 may image sample 1792 in a widefield configuration without departing from the scope hereof.

A distinctive feature imaging system 1700 is the ability to measure analyte in aqueous solution, placed in a Petri dish or microwell plate, where the depth of the aqueous solution is greater than 50 μm, which would lead to strong attenuation of mid-IR light travelling through water and thus impedes any transmission measurement in the mid-infrared. This is achieved by placing the analyte directly on top of plasmonic nanostructure 1794, and having the incident light incident on plasmonic nanostructure 1794 (through objective 1726) from the bottom through a mid-infrared transparent substrate, and collecting the reflected beam through objective 1726. The mid-infrared transparent substrate may be part of plasmonic nanostructure 1794, as an example of substrate 1210.

By doing so, analytes on top of plasmonic nanostructure 1794 sample may be imaged through its interaction with plasmonic nanostructure 1794. Here, we focus the optical beam 1712 to image plasmonic nanostructure 1794 instead of the analyte. The analyte interacts with plasmonic nanostructure 1794 through its interaction with the plasmonic hotspots, resulting in a modulation of the reflectance of plasmonic nanostructure 1794, either due to the molecular vibrational bands of the analyte (which leads to absorption in the mid-infrared band) or due to the shift of plasmonic nanostructure 1794's resonance as a result of the refractive index of the analyte being either higher or lower than that of the surrounding medium. This results in a localized modulation of plasmonic nanostructure 1794's reflectance (localized in a sense that within a large nanoantenna array, modulation in reflectance only occurs at spatial locations where the analyte interacts with one or more nanoantennas), and this reflectance is measured.

In embodiments, imaging system 1700 requires the analyte to interact with at least one nanoantenna in an array of nanoantennas (of plasmonic nanostructure 1794), and the spatial feature of the analyte should be smaller than the size of the nanoantenna array (of plasmonic nanostructure 1794), so that there is reflectance variation across the different nanoantennas within an array. In at least this aspect, imaging system 1700 differs from conventional methods. Such methods include measuring the IR spectrum of an analyte that uniformly covers several nanostructure pixels, defined as array of multiple nanostructures, with each nanostructure pixel possessing a unique optical resonant frequency. In contrast, embodiments of imaging system 1700 image analyte spatial features interacting with just a few nanostructure units (periods of array 1280) ranging from one nanostructure (period of array 1280), and up to the entire array.

Another important feature of imaging system 1700 that that it allows for this reflection-based measurement with light at normal incidence (along axis A3), and the objective placed directly below sample 1792. The direction of light propagation may deviate slightly from normal incidence. For example, the angle of incidence with respect to axis A3 may be less then ten degrees, for example, less than five degrees or less than two degrees. In case an objective lens is used to focus the light onto the nanostructure 1794, what is meant by normal incidence is that the chief ray passing through the center of the objective lens is normally incident onto the nanostructure 1794.

This normal or near-normal incidence is in contrast with setups using attenuated total reflection, in which either single-bounce or multi-bounce internal reflection elements (IRE, also simply called prisms) are used. Multi-bounce prisms make the setup unsuitable for imaging applications since it spreads out light interaction with analyte over a large area. Although single bounce prisms can be used for imaging, light needs to be incident at an angle. Imaging system 1700 allows for normal-incidence imaging, which reduces image artifacts, and also is more suitable for high-throughput imaging.

In contrast in photothermal microscopy systems that use a probe beam in the visible band, embodiments of imaging system 1700 uses only light in the mid-infrared band (e.g. optical beam 1712), which simplifies the optical setup. In addition, the direct measurement of mid-infrared reflectance allows us to use smaller light intensity, which alleviates concerns for phototoxicity.

An analyte may be placed in a dish/micro-well, directly on top of plasmonic nanostructure 1794, and immersed in a deep layer of water. The depth may exceed 50 μm, which is deep enough that mid-infrared light is strongly attenuated, making transmission measurement impractical. Imaging system 1700 may capture images in reflectance mode using imaging objective 1726 from below, where the light goes through substrate 1791, is reflected at plasmonic nanostructure 1794, and propagates through substrate 1791 again.

Figure 18:
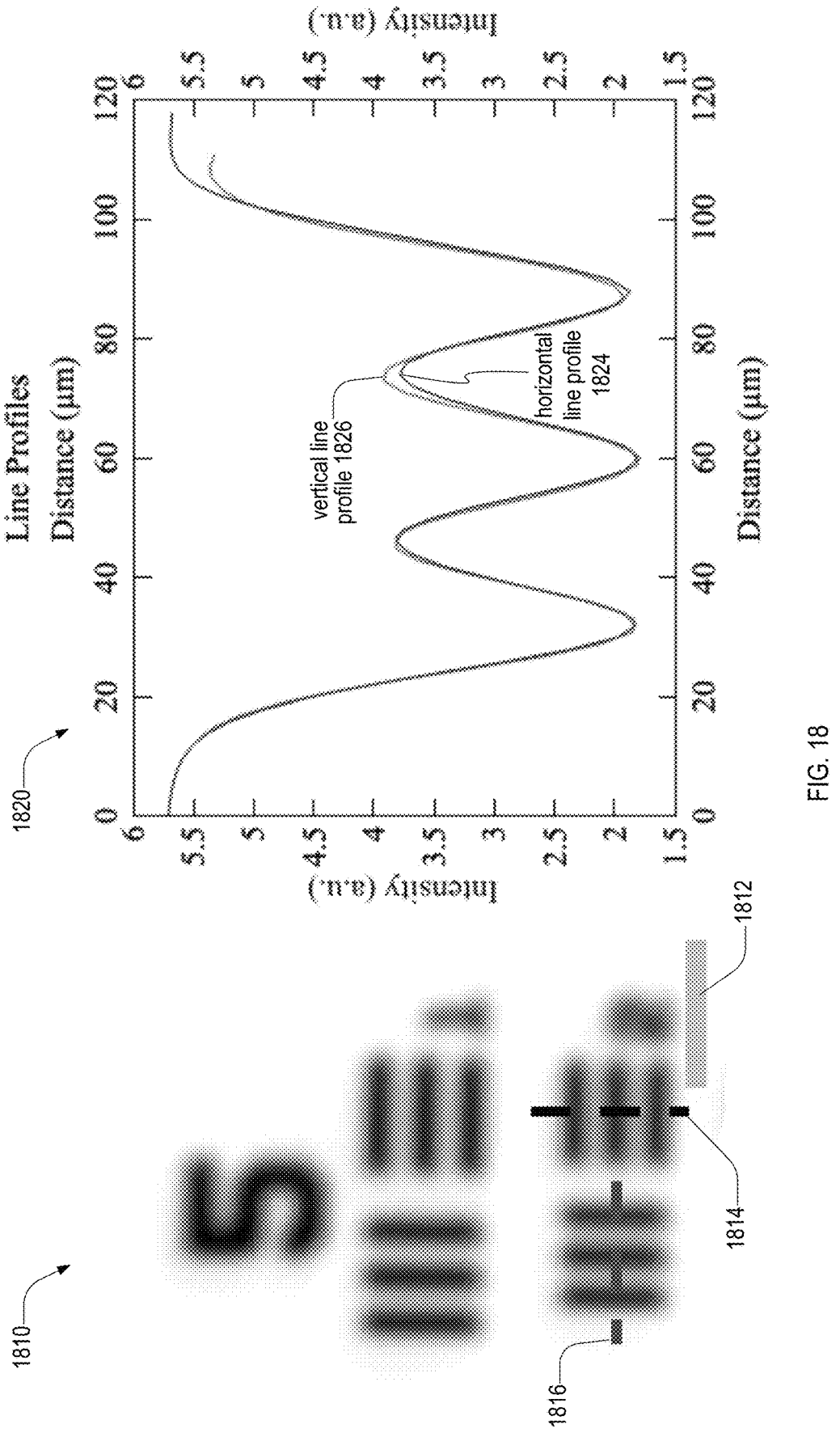
FIG. 18 is a resolution target test with a negative 1951 USAF test target and line profiles of the USAF test target element imaged by the imaging system of FIG. 17.

FIG. 18 shows results resolution target test. FIG. 18 includes a test target 1810, which is a negative 1951 USAF test target (R3L3S1N, Thorlabs Inc., NJ, USA) at λ=6.21 μm. Test target 1810 is annotated with a vertical line 1814 and a horizontal line 1816 at target element 5-2, which have a 13.92-μm linewidth. A scale bar 1812 denotes a length 100 μm. A plot 1820 shows line profiles 1824 and 1826 corresponding to lines 1814 and 1816, respectively at λ=6.21 μm. The target element 5-2 is clearly resolved.

Figure 19:
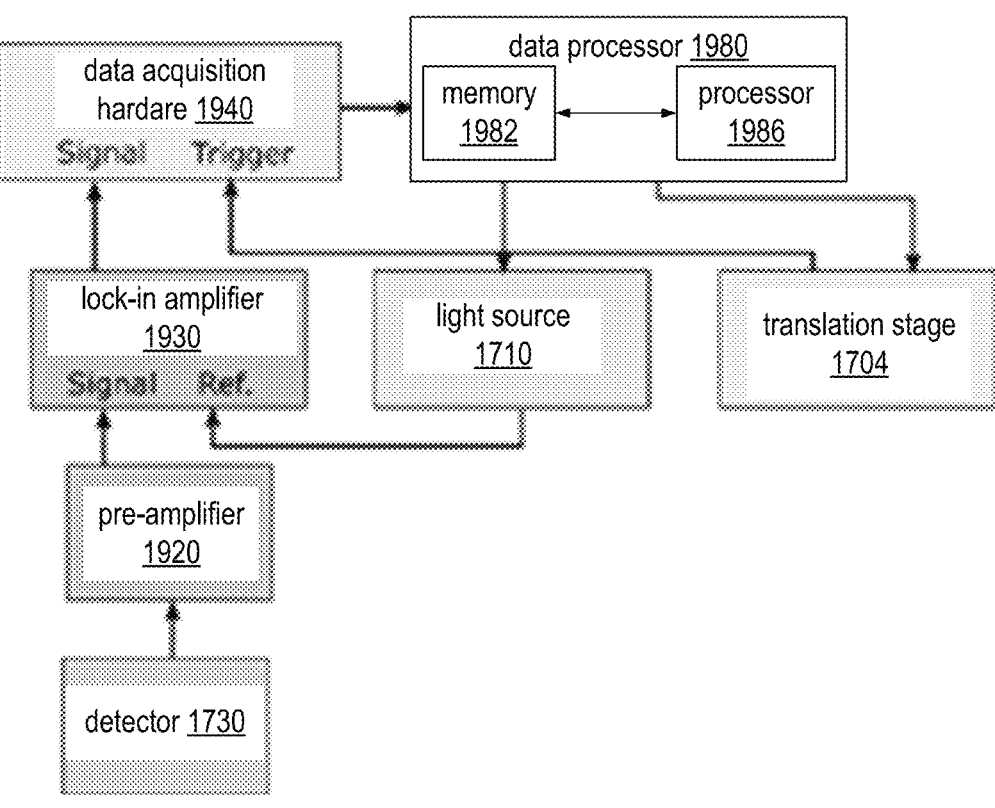
FIG. 19 is a schematic of electronics, which is part of embodiments of the imaging system of FIG. 17.

FIG. 19 is a schematic of hardware 1900, which is part of embodiments of imaging system 1700. Hardware 1900 includes parts of imaging system 1700 introduced in the description of imaging system 1700: translation stage 1704, light source 1710, and detector 1730. Hardware 1900 may also include at least one of a pre-amplifier 1920, a lock-in amplifier 1930, data acquisition hardware 1940, and a data processor 1980.

Data processor 1980 may be communicatively coupled to at least one of light source 1710 and translation stage 1704. Data processor 1980 include a memory 1982 and a processor 1986. Memory 1982 stores machine-readable instructions that, when executed by processor 1986, control processor 1986 the implement the functionality of hardware 1900 and/or imaging system 1700. Data acquisition hardware 1940 may be part of data processor 1980.

Detector 1730 is communicatively coupled to lock-in amplifier 1930 either directly or via pre-amplifier 1920. Lock-in amplifier 1930 has a signal port and a reference port, which are communicatively coupled to pre-amplifier 1920 (or detector 1730) and light source 1710, respectively. Data acquisition hardware 1940 has a signal port and a trigger port, which are communicatively coupled to lock-in amplifier 1930 and translation stage 1704, respectively.

Detector 1730 may have a one-microsecond time constant. Pre-amplifier 1920 may have a 150-kHz bandwidth. A maximum reference frequency of lock-in amplifier 1930 may be 102 KHz. Light source 1710 may be operated at a repetition rate in the range of 100 kHz and 2 MHz. A maximum speed of translation stage 1704 may be two millimeters per second.

FIG. 19 denotes example values of the following quantities associated with hardware of hardware 1900: a reference frequency, bandwidth, time constant, repetition rate, and maximum speed.

2.2 Fabrication of the Nanostructure Arrays

The π-shaped plasmonic nanoantennas of inset 1780 were written by e-beam lithography (JBX9500FS Electron Beam Lithography System, JEOL USA Inc., MA, USA) on a 12.5 mm×12.5 mm×0.5 mm IR-transparent $CaF_2$ substrate and they formed an array of 300 μm×300 μm (the nanostructure array). After the development, 5 nm of chromium and 70 nm of gold was deposited to be the body of the nanostructures. See FIG. 17 for the scanning electron microscope (SEM) image of the nanoantennas. Each nanoantenna's unit cell dimension was approximately 1.458 μm×1.701 μm (width× length), and there were 205×176 of nanoantennas in each array.

2.2 Fixed Cells and Single-Cell Spectroscopy

Human epidermoid carcinoma cell line A431 (acquired from the American Type Culture Collection) were trypsinized from culture flask and seeded sparsely on the nanostructure in Dulbecco's Modified Eagle Medium (DMEM) supplemented by 10% fetal bovine serum. The cells on nanostructure were incubated in standard incubator overnight to allow for cell adhesion and spreading. Cells were then fixed with 10% formalin solution for fifteen minutes and washed with phosphate-buffered saline (PBS). The fixed cell on nanostructure sample was subsequently imaged in PBS using the setup in FIG. 17. The reflectance of a cell on the nanostructure $R_{cell}(\omega)$ is defined as the following:

$$R_{cell}(\omega) = V_{cell}(\omega)/V_{no-cell}(\omega), \tag{2}$$

where the ω is the frequency, $V_{cell}(\omega)$ is the frequency-dependent reflective signal amplitude (in volts) of a cell on the nanostructure, and $V_{no-cell}(\omega)$ is the frequency-dependent reflective signal amplitude (in volts) of the nanostructure not covered by any cell.

The obtained spectra were post-processed to remove the artefacts. The Fabry-Perot effect was taken care of by a band-pass filter and spikes in the spectrum due to water vapor were removed through interpolation.

2.3 Live Cell Adhesion

We observed the process of live human epidermoid carcinoma cell line A431 (acquired from the American Type Culture Collection) adhering to the nanostructure with our setup by taking snapshots at a certain time gap. The cells were trypsinized from the flask, centrifuged, extracted from sediment, then suspended in serum-free Leibovitz's L-15 medium. 100 μL of L-15 was added to the nanostructure-bottomed well with no cell coverage. Before the beginning of the experiment, a reference Amide II map was captured. At the beginning of the experiment, 100 μL of the cell suspension was added to the well and we simultaneously started the image acquisition.

2.4 Image Processing

Figure 20:
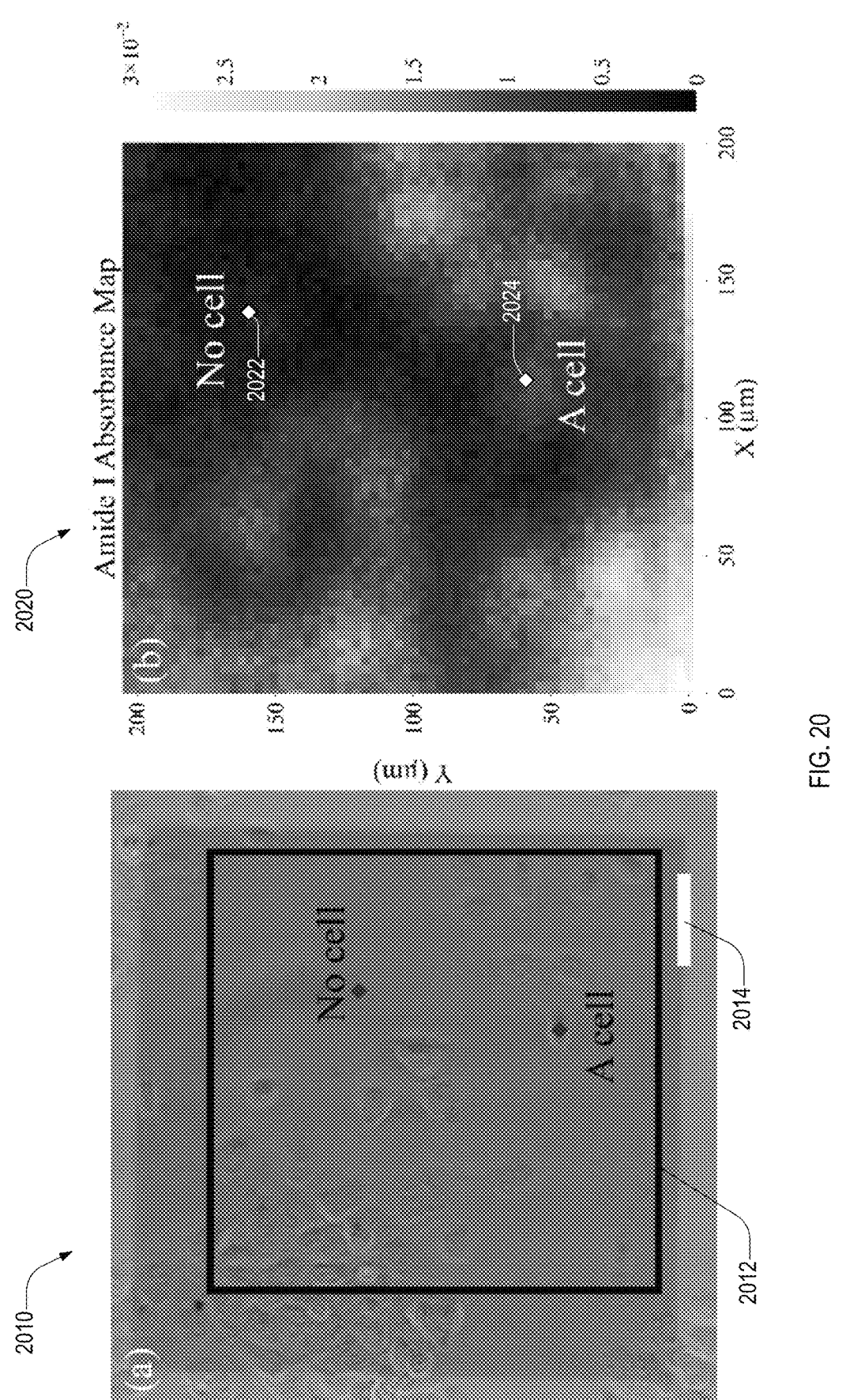
FIG. 20 includes microscopy images of fixed cells in water within a scanning area of the imaging system of FIG. 17 and an absorbance map of Amide cells within the scanning area.

FIG. 20 includes a phase contrast image 2010 and an absorbance map 2020 of fixed cells in water within a scanning area 2012 of imaging system 1700 and an absorbance map of Amide cells within the scanning area. Phase contrast image 2010 is of fixed cells in water. The shaded area was the nanostructure array. The black square indicates the QCL microscope's scanning area 2012. A scale bar 2014 is 50-μm long. Absorbance map 2020 is that of Amide I (1,660 cm$^{-1}$) in scanning area 2012. White diamonds 2022 and 1924 indicate the pixels used for QCL spectroscopy.

Herein we present two types of IR image. One is the single-band absorbance map $A_{band}(x, y)$:

$$A_{band}(x, y) = -\log_{10}[R_{band}(x, y)], \qquad (3)$$

where the reflectance map $$R_{band}(x, y) = V_{band}(x, y)/\max(V_{band}(x, y)), \qquad (4)$$

$V_{band}(x, y)$ is the positional reflective signal amplitude (in volts) of the scanning area on the nanostructure. The maximum of $V_{band}(x, y)$ is used as the background to calculate the reflectance, as this corresponds to the brightest position with no cells. The absorbance map is used to quickly determine where the cells are, so we could further perform single-cell spectroscopy.

Figure 21:
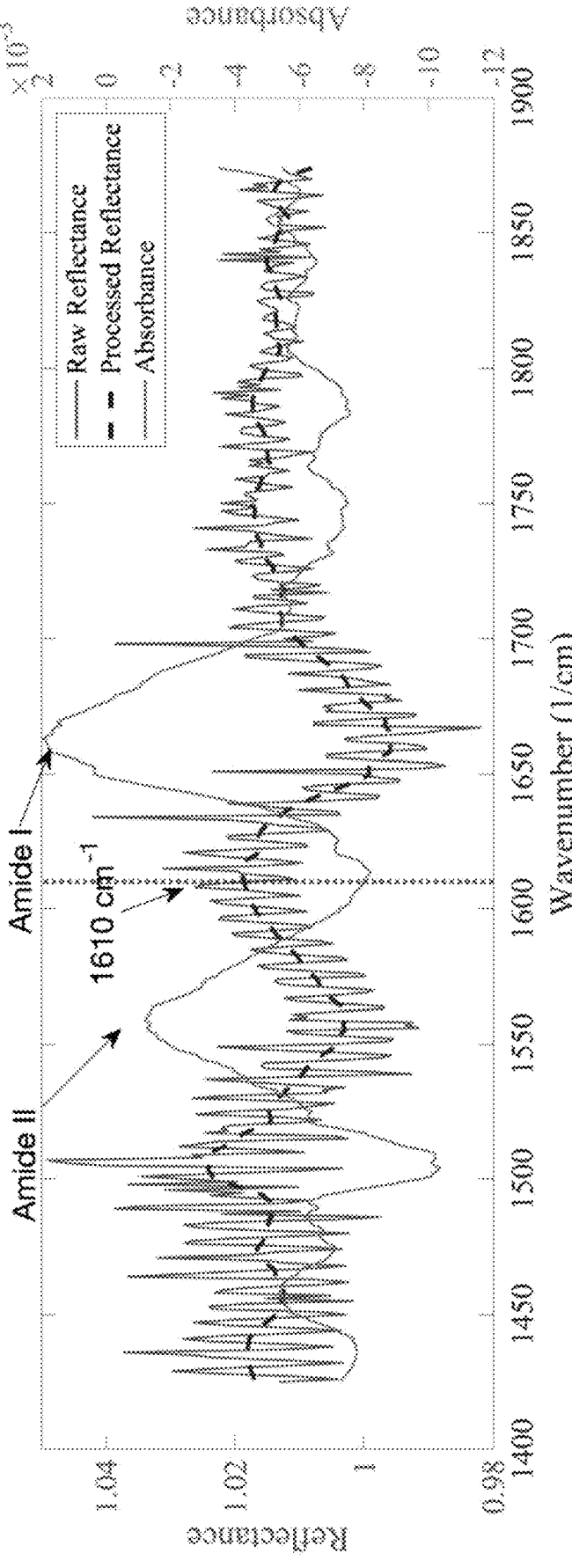
FIG. 21 is a single cell reflectance spectrum captured by the imaging system of FIG. 17.

FIG. 21 is a single cell reflectance spectrum captured by imaging system 1700. A cell had two strong absorbance peaks at Amide I (1,660 cm$^{-1}$) and Amide II (1,550 cm$^{-1}$) and none in-between. 1,610 cm$^{-1}$ was used as the background.

To obtain high quality images, further background correction is required. Based on the fabrication quality, the nanostructure resonance could have slight deviation depending on the position, and this would appear as a changing background signal. From the single-cell spectroscopy in FIG. 21, we knew that a cell had two strong absorbance peaks at Amide I (1,660 cm$^{-1}$) and Amide II (1,550 cm$^{-1}$) and none in-between. We took an image with 1,610 cm$^{-1}$ and used it to correct for the background drift in the image.

The corrected absorbance map for a specific band $$A_{corrected}(x, y) = -\log_{10}[R_{band}(x, y)/R_{off-band}(x, y)], \qquad (5)$$

where both the reflectance map of the band $R_{band}(x, y)$ and the reflectance map of the background $R_{off-band}(x, y)$ (Here, 1,610 cm$^{-1}$ was used.) are defined in a similar fashion as Eq. (4). This correction is analogous to the baseline correction typically used in FTIR spectroscopy.

2.5 Results

Fixed-Cell MIR Imaging and Single-Cell MIR Spectroscopy

Few have shown MIRCI on fixed cells in water. In FIG. 20, the fixed cell clusters scattered around the nanostructure (shaded square area). We selected the area with the most isolated cells (marked in a black square) and conducted a point-to-point scan at Amide I (1,660 cm$^{-1}$). The Amide I absorbance map was plotted in absorbance map 2020. Finally, a point of nanostructure without cell coverage and a point on an isolated cell were chosen (marked in blue diamonds) for single-cell spectroscopy (shown in FIG. 21).

Figure 22:
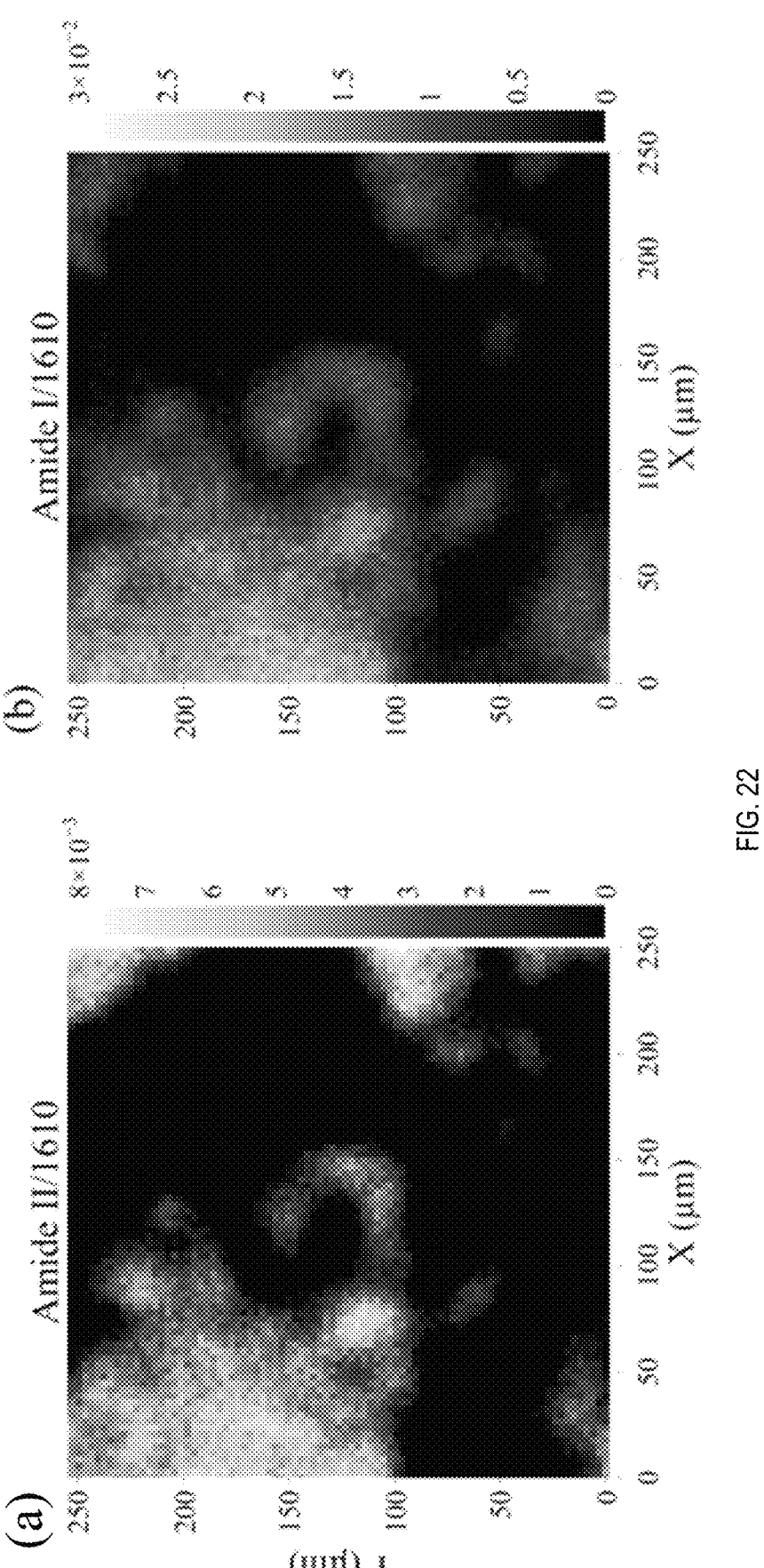
FIG. 22 includes images of Amide I and Amide II captured by the imaging system of FIG. 17.

The corrected IR absorbance images of the whole nanostructure array (shaded area in FIG. 20) are shown in FIG. 22. FIG. 22 (a) shows an image of Amide II (1,550 cm$^{-1}$) absorbance map divided by the background map (1,610 cm$^{-1}$). FIG. 22 (b) shows the image of Amide I (1,660 cm$^{-1}$) absorbance map divided by the background map (1,610 cm$^{-1}$). The uncorrected IR absorbance image in FIG. 20(b) showed rather poor agreement with the phase contrast image 2010. The lower half of absorbance map 2020 was overly illuminated in intensity because the nanostructure had higher reflectivity (due to the fabrication quality) in the region. This could be corrected by image subtraction with Eqn. 5. The corrected IR absorbance images shown in FIG. 22 had better agreement of cellular distribution with the phase contrast image 2010.

The center cell cluster (a crescent-shaped cluster located around X=70-150 μm, Y=100-650 μm) was much better resolved in FIG. 22 (a) than in FIG. 22 (b). The Amide II (1,550 cm$^{-1}$) intensity did not saturate in the gaps between cells as much as Amide I (1,660 cm$^{-1}$). The lower right corner cell cluster (a triangular-shaped cluster located around X=150-250 μm, Y=0-120 μm) was also better resolved. Four cells were resolved on the lower half of the triangle in both FIGS. 22 (a) and (b), but the middle two cells (at X=200 μm, Y=40-70 μm) stuck together in FIG. 22.

Capturing Live Cell Adhesion with MIR Imaging

Figure 23:
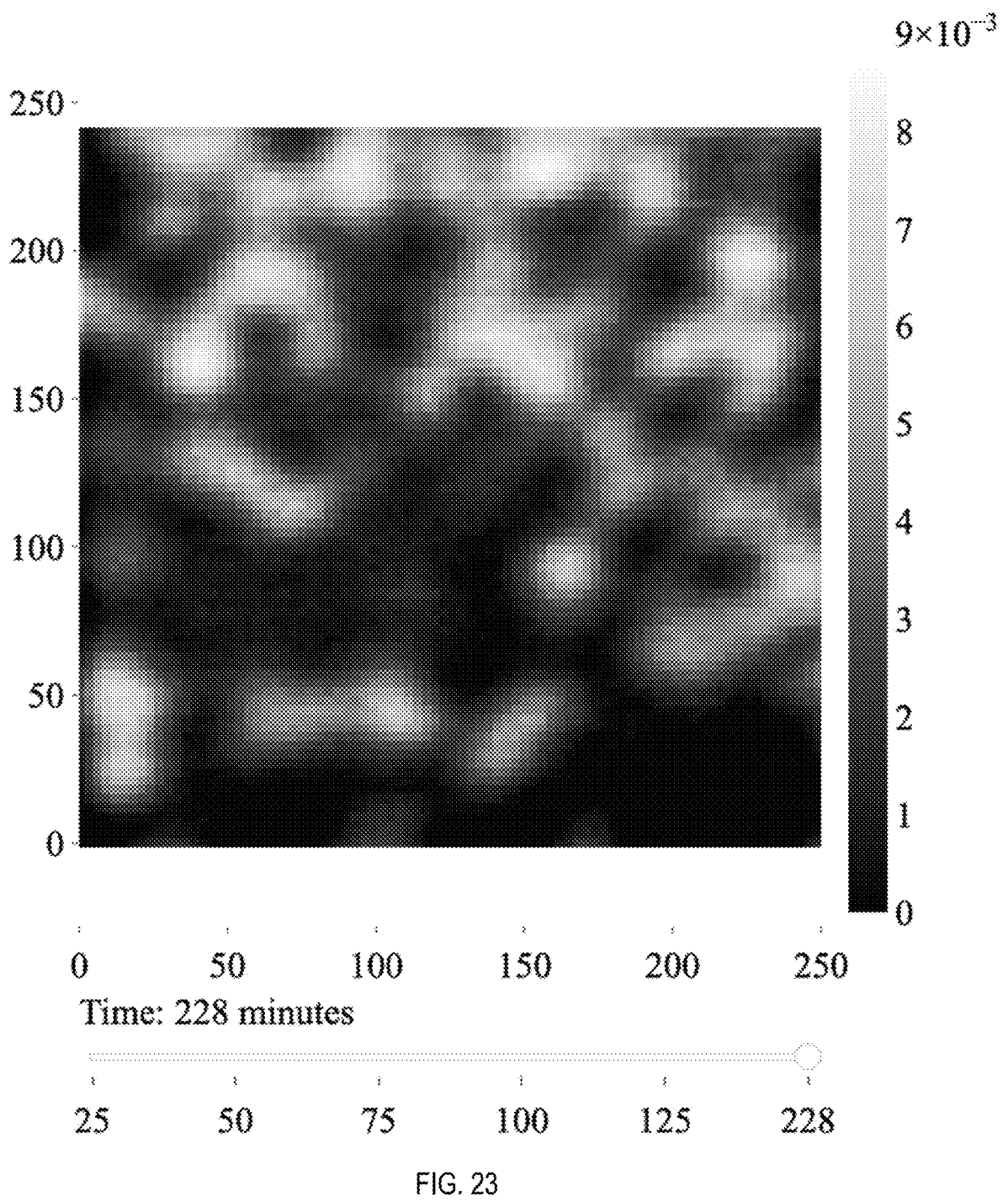
FIG. 23 is an image showing cell adhesion of Amide II on a plasmonic nanostructure of FIG. 12 as imaged by an embodiment of the imaging system of FIG. 17.

In this section, we demonstrate a proof of concept of MIRCI capturing live cell activities through Amide II (1,550 cm$^{-1}$) map. We recorded the process of live cells adhering the nanostructure. In the beginning, live cells in suspension were added to the well and they sedimented gradually due to the gravity. In the first 125 minutes, only a small portion of the cells adhered the nanostructure. At the 228$^{th}$ minute (shown in FIG. 23), a large portion of cells adhered to the nanostructure. This demonstrates that the cells were viable and could adhere to the nanostructure, despite of the constant IR illumination from the bottom and the plasmonic hotspots produced by the nanostructure.

Imaging System

Figure 24:
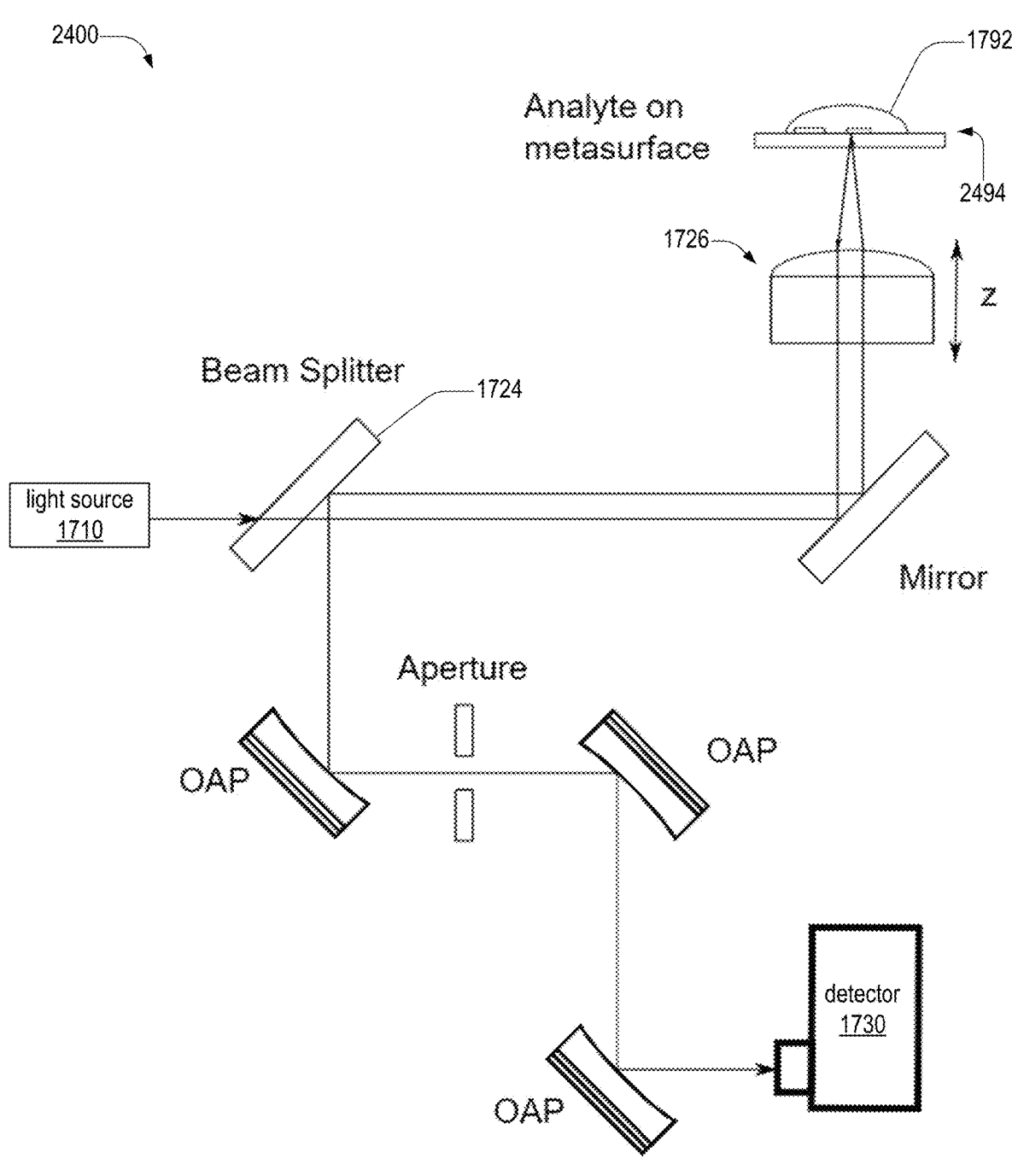
FIG. 24 is a schematic of a system that images a sample adhered to a plasmonic nanostructure of FIG. 12, in an embodiment.

FIG. 24 is a schematic of an imaging system 2400. Imaging system 2400 includes at least one of a plasmonic nanostructure plasmonic nanostructure 2494, translation stage 1704, light source 1710, beam splitter 1724, imaging objective 1726, and detector 1730. Plasmonic nanostructure 2494 is an example of plasmonic nanostructure 1200.

Plasmonic nanostructure 2494 on top of (or includes) a substrate wherein sample 1792 is attached, adhered or close to the top of plasmonic nanostructure 2494. Light source 1710 provides infrared light to sample 1792, which may include an analyte and/or an object. The infrared light propagates through the substrate as an incident light to sample 1792 and is at least partially reflected by plasmonic nanostructure 2494 and sample 1792 as a reflected signal.

Beam splitter 1724 separates the incident light to sample 1792 and reflected light from plasmonic nanostructure 2494 and sample 1792. The reflected signal propagates away from plasmonic nanostructure 2494, back through imaging objective 1726, and to beam splitter 1724, which reflects the reflected signal to detector 1730 for imaging. Imaging system 2400 may include one or more off-axis parabolic mirrors (OAPs) along a beam path between plasmonic nanostructure 2494 and detector 1730./

Example Enumerated Embodiments

Features described above as well as those claimed below may be combined in various ways without departing from the scope hereof. The following enumerated examples illustrate some possible, non-limiting combinations Embodiment 1. A system for imaging an analyte or an object in a sample comprising: a plasmonic nanostructure (e.g. a plasmonic metasurface, an elevated nanograting structures, or any one of the plasmonic nanostructure as described in the present application) on top of a substrate wherein the analyte or the object is attached, adhered or close to the top of the plasmonic nanostructure; a light source configured to provide infrared light to the sample comprising the analyte or the object, wherein the infrared light transmits the substrate as an incident light to the sample and at least partially reflect by the plasmonic nanostructure and the analyte or the object close to the plasmonic nanostructure; a beam splitter configured to separate the incident light to the sample and reflected light from the plasmonic nanostructure or close to the plasmonic nanostructure; and an objective wherein the incident light incident onto the nanostructure through the objective below the substrate and the reflected light transmit through the substrate back to the objective; and a detector configured to collect the reflected light separated by the beam splitter for imaging.

Embodiment 2. The system of embodiment 1, wherein the light source is a narrow band mid-infrared light source having a full width at half maximum (FWHM) of no more than 5 cm$^{-1}$, e.g. 0.1-5 cm$^{-1}$, including any value therewithin or any subranges therebetween.

Embodiment 3. The system of embodiment 1, wherein the light source is tunable.

Embodiment 4. The system of embodiment 1, wherein the light source is selected from a quantum cascade laser (QCL) or an optical parametric amplifier (OPA).

Embodiment 5. The system of embodiment 1, wherein the light source is a mid-infrared light source to provide light having wavelengths between 2.5 to 25 µm, including any value therewithin or any subranges therebetween.

Embodiment 6. The system of embodiment 1, wherein the substrate is infrared transparent.

Embodiment 7. The system of embodiment 1, wherein the substrate is mid-infrared transparent.

Embodiment 8. The system of embodiment 1, wherein the substrate is part of a container for holding a liquid solution and the sample is in the liquid solution.

Embodiment 9. The system of embodiment 1, wherein the sample is in a liquid solution during imaging.

Embodiment 10. The system of embodiment 1, wherein the sample is in an aqueous solution having a depth of greater than 50 µm, e.g. 50 µm-100,000 µm, including any value therewithin or any subranges therebetween.

Embodiment 11. The system of embodiment 1, wherein the object is a cell.

Embodiment 12. The system of embodiment 1, wherein the object is a living cell or a fixed cell.

Embodiment 13. The system of embodiment 1, wherein the substrate is part of a bottom material or surface of a well, a dish, or a container.

Embodiment 14. The system of embodiment 1, wherein the substrate is put on bottom of a Petri dish, a flow chamber, a microfluidic device, or a multi-well plate.

Embodiment 15. The system of embodiment 1, wherein the objective is configured to operates at mid-infrared.

Embodiment 16. The system of embodiment 1, wherein the objective is a reflective Cassegrain objective or a refractive objective.

Embodiment 17. The system of embodiment 1, wherein the objective is a chalcogenide refractive objective.

Embodiment 18. The system of embodiment 1, wherein the analyte or the object interacts with the plasmonic nanostructure to modulate the reflected light.

Embodiment 19. The system of embodiment 1, wherein the plasmonic nanostructure comprises one or more pillars or gratings, an array of pillars or gratings, or an array of nanoantenna. The nanostructure or nanoantenna may be resonant, non-resonant, flat, and/or elevated nanostructure or nanoantenna.

Embodiment 20. The system of embodiment 1, wherein the beam splitter is a CaF2 beam splitter.

Embodiment 21. The system of embodiment 1, wherein the substrate is an IR transparent CaF2 substrate.

Embodiment 22. The system of embodiment 1, further comprising a scanning system comprises a stage scanning module for coarse scanning and a point-scanning module or a galvanometer scanner for fine scanning.

Embodiment 23. The system of embodiment 1, further comprising an optical attenuator to reduce beam power of the light source.

Embodiment 24. The system of embodiment 1, wherein the light source is configured to an average power between 100 nW and 100 mW, including any value therewithin or any subranges therebetween.

Embodiment 25. The system of embodiment 1, further comprising a confocal pinhole on a reflected beam path to restrict out-of-plane light and stray light being collected by the detector.

Embodiment 26. The system of embodiment 25, wherein confocal pinhole has an aperture size between 10 µm and 1,000 µm, including any value therewithin or any subranges therebetween.

Embodiment 27. The system of embodiment 1, wherein the system is configured to focus the light beam to image a plane of the nanostructure or a plane close to the nanostructure.

Embodiment 28. The system of embodiment 1, wherein interaction between the light and the analyte or object is configured to be mediated by one or more nanostructures of the nanostructure resulting in a modulation of the reflectance.

Embodiment 29. The system of embodiment 28, wherein the modulation comprise the molecular vibrational bands of the analyte leads to absorption in an infrared band and a shift of resonant frequency of a nanostructure of the metasurface as a result of the refractive index of the analyte or the objective being either higher or lower than that of a surrounding medium.

Embodiment 30. The system of embodiment 1, wherein the analyte or the object interact with at least one nanoantenna in an array of nanoantennas, and a spatial feature of the analyte or the object is smaller than a size of the nanoantenna array such that there is a reflectance variation across different nanoantennas within the array.

Embodiment 31. The system of embodiment 1, wherein the light source is a broad band mid-infrared light source having a full width at half maximum (FWHM) of more than 5 cm$^{-1}$.

Embodiment 32. The system of embodiment 1, where the detector is a Fourier transform infrared spectrometer.

Embodiment 33. A method of using the system of any one of embodiments 1-33 for infrared chemical imaging of analyte or objective, especially in a liquid solution (e.g. an aqueous solution).

Changes may be made in the above methods and systems without departing from the scope of the present embodiments. It should thus be noted that the matter contained in the above description or shown in the accompanying drawings should be interpreted as illustrative and not in a limiting sense. Herein, and unless otherwise indicated the phrase "in embodiments" is equivalent to the phrase "in certain embodiments," and does not refer to all embodiments.

Herein, disclosure that a value of a quantity may be within a range of values means that the value of the quantity may be (i) any value therewithin and (b) within any subranges within the range. Example quantities include spatial dimensions (e.g., length, width, height, thickness) and material properties (e.g., density, conductivity, and refractive index).

Regarding instances of the terms "and/or" and "at least one of," for example, in the cases of "A and/or B" and "at least one of A and B," such phrasing encompasses the selection of (i) A only, or (ii) B only, or (iii) both A and B. In the cases of "A, B, and/or C" and "at least one of A, B, and C," such phrasing encompasses the selection of (i) A only, or (ii) B only, or (iii) C only, or (iv) A and B only, or (v) A and C only, or (vi) B and C only, or (vii) each of A and B and C. This may be extended for as many items as are listed.

The following claims are intended to cover all generic and specific features described herein, as well as all statements of the scope of the present method and system, which, as a matter of language, might be said to fall therebetween.

We claim:

1. A system for imaging an analyte or an object in a sample comprising:

a plasmonic nanostructure on top of a substrate and including an array of nanoantennas, wherein the analyte or the object is attached, adhered or close to the top of the plasmonic nanostructure;

a light source configured to provide infrared light to the sample comprising the analyte or the object, wherein the infrared light transmits the substrate as an incident light to the sample and at least partially reflect by the plasmonic nanostructure and the analyte or the object close to the plasmonic nanostructure;

a beam splitter configured to separate the incident light to the sample and reflected light from the plasmonic nanostructure or close to the plasmonic nanostructure;

an objective wherein the incident light incident onto the nanostructure through the objective below the substrate and the reflected light transmit through the substrate back to the objective; and a detector configured to collect the reflected light separated by the beam splitter for imaging wherein the analyte or the object interact with at least one nanoantenna in the array of nanoantennas, and a spatial feature of the analyte or the object is smaller than a size of the nanoantenna array such that there is a reflectance variation across different nanoantennas within the array.

2. The system of claim 1, wherein the light source is a narrow band mid-infrared light source having a full width at half maximum (FWHM) of no more than 5 cm$^{-1}$, or a broad band mid-infrared light source having a full width at half maximum (FWHM) of more than 5 cm$^{-1}$.

3. The system of claim 1, wherein the light source is selected from a quantum cascade laser (QCL) or an optical parametric amplifier (OPA).

4. The system of claim 1, wherein the substrate is part of a container for holding a liquid solution and the sample is in the liquid solution.

5. The system of claim 1, wherein the sample is in an aqueous solution having a depth of greater than 50 μm.

6. The system of claim 1, wherein the substrate is part of a bottom material of a well, a dish, or a container.

7. The system of claim 1, wherein the substrate is put on bottom of a Petri dish, a flow chamber, a microfluidic device, or a multi-well plate.

8. The system of claim 1, wherein the objective is a reflective Cassegrain objective or a refractive objective.

9. The system of claim 1, wherein the analyte or the object interacts with the plasmonic nanostructure to modulate the reflected light.

10. The system of claim 1, further comprising a scanning system comprises a stage scanning module for coarse scanning and a point-scanning module or a galvanometer scanner for fine scanning.

11. The system of claim 1, further comprising a confocal pinhole on a reflected beam path to restrict out-of-plane light and stray light being collected by the detector.

12. The system of claim 1, wherein the system is configured to focus the light beam to image a plane of the nanostructure or a plane close to the nanostructure.

13. The system of claim 1, wherein interaction between the light and the analyte or object is configured to be mediated by one or more nanostructured elements of the nanostructure resulting in a modulation of the reflectance.

14. The system of claim 13, wherein the modulation includes excitation of the molecular vibrational bands of the analyte, which leads to absorption in an infrared band and a shift of resonant frequency of a nanostructured element as a result of the refractive index of the analyte or the objective being either higher or lower than that of a surrounding medium.

15. The system of claim 1, where the detector is a Fourier transform infrared spectrometer.

16. The system of claim 1, wherein the plasmonic nanostructure includes:

a dielectric layer on the substrate wherein the substrate comprises a dielectric substrate;

an array of dielectric pillars on the dielectric layer, wherein the array is a periodic array or non-periodic array; and a respective conductive layer on each of the dielectric pillars of the array.

17. The system of claim 16, wherein each dielectric pillar of the array is (i) formed of the same material as the dielectric layer, and (ii) a protrusion of the dielectric layer extending away from the dielectric substrate such that (a) a top pillar-surface of each dielectric pillar of the array is a respective region of a top surface of the dielectric layer, and (b) its respective conductive layer is on the top pillar-surface.

18. The system of claim 16, wherein the dielectric substrate includes (i) a central substrate-region beneath the array and having a first substrate thickness, and (ii) a peripheral substrate-region surrounding the central substrate-region and having a second substrate thickness that exceeds the first substrate thickness.

19. The system of claim 18, wherein the first substrate thickness is equal to zero, such that the peripherical substrate-region defines an aperture through the dielectric substrate.

20. A system for imaging an analyte or an object in a sample comprising:

a plasmonic nanostructure on top of a substrate wherein the analyte or the object is attached, adhered or close to the top of the plasmonic nanostructure;

a light source configured to provide infrared light to the sample comprising the analyte or the object, wherein the infrared light transmits the substrate as an incident light to the sample and at least partially reflect by the plasmonic nanostructure and the analyte or the object close to the plasmonic nanostructure;

a beam splitter configured to separate the incident light to the sample and reflected light from the plasmonic nanostructure or close to the plasmonic nanostructure;

an objective wherein the incident light incident onto the nanostructure through the objective below the substrate and the reflected light transmit through the substrate back to the objective;

a detector configured to collect the reflected light separated by the beam splitter for imaging; and a confocal pinhole on a reflected beam path to restrict out-of-plane light and stray light being collected by the detector.

21. A system for imaging an analyte or an object in a sample comprising:

a plasmonic nanostructure on top of a dielectric substrate and including a dielectric layer on the dielectric substrate, an array of dielectric pillars on the dielectric layer; and a respective conductive layer on each of the dielectric pillars of the array, wherein the analyte or the object is attached, adhered or close to the top of the plasmonic nanostructure;

a light source configured to provide infrared light to the sample comprising the analyte or the object, wherein the infrared light transmits the dielectric substrate as an incident light to the sample and at least partially reflect by the plasmonic nanostructure and the analyte or the object close to the plasmonic nanostructure;

a beam splitter configured to separate the incident light to the sample and reflected light from the plasmonic nanostructure or close to the plasmonic nanostructure;

an objective wherein the incident light incident onto the nanostructure through the objective below the dielectric substrate and the reflected light transmit through the dielectric substrate back to the objective; and a detector configured to collect the reflected light separated by the beam splitter for imaging.

* * * * *